United States Patent
Moon et al.

(10) Patent No.: US 10,688,189 B1
(45) Date of Patent: Jun. 23, 2020

(54) MODULATED GUANIDINE-CONTAINING POLYMERS OR NANOPARTICLES

(71) Applicants: Joong Ho Moon, Weston, FL (US); Alfonso Barrios, Miami, FL (US)

(72) Inventors: Joong Ho Moon, Weston, FL (US); Alfonso Barrios, Miami, FL (US)

(73) Assignee: THE FLORIDA INTERNATIONAL BOARD OF TRUSTEES, Miami, FL (US)

( * ) Notice: Subject to any disclaimer, the term of this patent is extended or adjusted under 35 U.S.C. 154(b) by 0 days.

(21) Appl. No.: 16/799,375

(22) Filed: Feb. 24, 2020

Related U.S. Application Data

(63) Continuation-in-part of application No. 16/220,801, filed on Dec. 14, 2018, now Pat. No. 10,568,902.

(60) Provisional application No. 62/598,578, filed on Dec. 14, 2017.

(51) Int. Cl.
| | |
|---|---|
| *A61K 31/785* | (2006.01) |
| *A61K 47/54* | (2017.01) |
| *A61P 35/00* | (2006.01) |
| *A61K 47/32* | (2006.01) |
| *C08F 34/02* | (2006.01) |
| *C07D 491/18* | (2006.01) |

(52) U.S. Cl.
CPC ............ *A61K 47/32* (2013.01); *C07D 491/18* (2013.01); *C08F 34/02* (2013.01)

(58) Field of Classification Search
CPC ............................. A61K 31/785; A61K 47/545
See application file for complete search history.

(56) References Cited

PUBLICATIONS

Miel, H., et al., "Conversion of N,N'-bis(tert-butoxycarbonyl)Guanidines to N-(N'-tert-butoxycarbonylamidino)Ureas." Tetrahedron Letters, Mar. 1998, 39(12): 1565-1568.

Mitchell, L.A., et al., "A comparison of 3,4,6a,7,10,10a-hexahydro-7,10-epoxypyrimido[2,1-a]isoindol-6(2H)-one and 2-(2-aminoethyl)-3a,4,7,7a-tetrahydro-1H-4,7-epoxyisoindole-1,3(2H)-dione: structural and reactivity differences of two homologous tricyclic imides." Acta Crystallographica Section C: Crystal Structure Communications, 2013, 69(6): 638-641.

Sgolastra, F., et al., "Sequence segregation improves non-covalent protein delivery." Journal of Controlled Release, 2017, 254: 131-136.

Tezgel, O., et al., "Cell penetrating peptide mimics prepared by ROMP." Abstracts of Papers of the American Chemical Society. vol. 240. 1155 16th ST, NW, Washington, DC 20036 USA: Amer Chemical Soc, 2010, 51(2): 94-95.

Tezgel, A.O., et al., "Synthetic Protein Mimics for Functional Protein Delivery." Biomacromolecules, 2017, 18(3): 819-825.

*Primary Examiner* — Kyle A Purdy
(74) *Attorney, Agent, or Firm* — Saliwanchik, Lloyd & Eisenschenk

(57) ABSTRACT

A modulated guanidine substituted polymer or nanoparticle has a guanidine moiety or on a plurality of repeating units of a polymer or on the surface of a nanoparticle where the guanidine moiety is modulated as a substituted amidinourea or amidinocarbamate or salt thereof. The modulated guanidine substituted polymer or nanoparticle can be prepared by direct amination of a N-Boc protected guanidine substituted conjugated polymer or N-Boc protected guanidine substituted nanoparticle, where an amine or alcohol is combined in solution or suspension with the protected conjugated polymer or nanoparticle and the resulting mixture is heated. The modulated guanidine substituted polymer or nanoparticle can be used in a cancer treatment formulation.

20 Claims, 18 Drawing Sheets

*compared with siRNA alone

MODULATED GUANIDINE-CONTAINING POLYMERS OR NANOPARTICLES

CROSS-REFERENCE TO A RELATED APPLICATION

This application is a continuation-in-part (CIP) application of U.S. application Ser. No. 16/220,801, filed Dec. 14, 2018, which claims the benefit of U.S. Provisional Application Ser. No. 62/598,578, filed Dec. 14, 2017, the disclosure of which is hereby incorporated by reference in its entirety, including all figures, tables and drawings.

GOVERNMENT SUPPORT

This invention was made with government support under DMR1352317 awarded by the National Science Foundation. The government has certain rights in the invention.

BACKGROUND OF INVENTION

Ovarian cancer (OVCA) is the most lethal gynecologic malignancy. The majority of patients are diagnosed with advanced disease, which ultimately recurs, and they die from the disease. OVCA is becoming resistant to current chemotherapies, including the two most commonly used first-line drugs taxol and cisplatin, and patients are exhausting their treatment options.

Multidrug resistance (MDR) is closely related to overexpression of membrane efflux proteins (e.g., P-glycoprotein) and anti-apoptotic proteins [e.g., survivin and myeloid cell leukemia 1 (Mcl-1)]. Because small RNA molecules, including small interfering RNA (siRNA), have an extraordinary ability to knock down gene expression, RNA interference (RNAi) induced by small RNA molecules can be an excellent solution for overcoming MDR.

RNA molecules are highly susceptible to enzymatic degradation and too big to penetrate the cellular membranes. Although various types of delivery materials have been developed and used at the in vitro tissue culture level, gene regulation at the ex vivo or in vivo level has been largely unsuccessful due to poor intracellular siRNA availability.

Lack of targeting and inefficient intracellular entry of drugs requires over dosing, which is also responsible for poor therapeutic outcomes. Efficient delivery of negatively charged RNA molecules to target cells is pivotal for a successful application of RNAi technology. Innovative therapeutic delivery techniques are urgently needed to address the drug resistance and poor intracellular entry efficiency.

In human airway epithelium possessing additional extracellular barriers, such as mucus layers, transfection using conventional lipid-based or positively charged carriers is extremely limited. As the critical physical barrier interfacing environmental stimuli, the mucosal surfaces of epithelium tightly regulate various physiological and immunological processes. In the mucus layer, dense mucin fibers and negatively charged proteoglycans provide the adhesive and viscous protective layer that often trap and remove positively charged carriers, resulting in poor delivery of payloads to the underlying epithelial cells. Very few options are currently available for delivering nucleic acids to the airway epithelium. Mucus-altering or mucolytic agents can be used as adjuvants of gene carriers, although high millimolar concentrations are often needed to disrupt or disturb the mucus layers.

Alternatively, block copolymers of polyethyleneimine (PEI) and polyethyleneglycol (PEG) have been developed to deliver plasmid DNA (pDNA) to the lung airways. Positively charged PEI and negatively charged pDNA form ionic complexes, while the PEG block shields the positively charged block from the negatively charged mucus layers and provides diffusion through nanometer sized mucus meshes. However, the PEG block often causes poor gene complexation and reduced cellular entry; and pDNA can form smaller ionic complexes with PEI-PEG copolymers due to the molecular topography of pDNA, enabling compaction to nanoparticles. Although optimization provides the opportunity to balance the ratios between charged and PEG segments, block copolymer architectures in biological fluids containing ions and proteins complicate surface properties and influence biological functions.

Short peptides or their synthetic mimics of the protein's translocation domains are excellent materials to introduce therapeutic agents to intracellular compartments rapidly. The fast entry of those materials is associated with a combination of membrane pore formation and non-receptor-mediated endocytosis. Combinations of ionic bonding, hydrogen bonding, and hydrophobic interactions influence the entry pathways. However, coupling cell penetrating peptides to therapeutic proteins or nucleic acids often alters the entry pathways, resulting in decreased intracellular availability. Fluorescent labels needed to study the entry mechanism and the localization of synthetic materials influence the material's physical properties and cellular behaviors toward the materials. The development of nontoxic biomaterials exhibiting superior cellular entry and therapeutic delivery is needed to substantially increase therapeutic efficacy of these systems.

In another approach, nanometer sized particles accumulate in relatively loosely organized tumor tissues as opposed to tight normal tissue. When the particulates are modified with ligands specific to the receptors overexpressed on cancer cell surfaces, targeting at the tissue level can be further improved. Unfortunately, overall therapeutic efficacy remains unsatisfactory due to poor intracellular entry and a lack of organelle targeting. Endocytosis mediated by cell surface receptors is the primary entry pathway, but it is often slow and inefficient. Endocytosed therapeutic agents undergo degradation in endosomes and lysosomes or in recycling processes, such as exocytosis, which lower the intracellular concentration of therapeutic agents. By not involving an endosome escaping process, direct membrane translocation offers high intracellular concentrations of therapeutics. Nanometer sized particles with modulated surface properties are pivotal for efficient intracellular delivery and labeling because the surface properties are closely related to their initial interaction following entry.

Aromatic π-electron conjugated polymers (CPs) are innovative fluorescent materials that have a high potential as therapeutic carriers. Because of excellent photophysical properties, such as high brightness and sensing ability, and excellent biophysical properties, such as biocompatibility, nontoxicity, high cellular interaction, and ease of entry, CPs have been used for live cell and tissue imaging, biochemical sensing, and gene and drug delivery. In addition to intrinsic fluorescent properties that are highly advantageous for labeling and tracking, the charged CPs are structurally similar in charge density and backbone rigidity to materials known for exhibiting efficient cellular entry, such as tyrosine aminotransferase (TAT) as shown in FIG. 1. Because of a rigid hydrophobic backbone and a flexible hydrophilic charged side chains, CPs can bind to and enter through cellular membranes.

Moon et al. U.S. Pat. Nos. 9,676,886 and 9,757,410 disclose biodegradable CPs that are made by introducing flexible degradable functional groups along the backbone of the CP that can be used for quantitative labeling of mitochondria. Cellular interaction and internalization of CPs are dependent on the chemical structures of both the backbone and side chains of the CPs. CPs with guanidine units (G-CPs) having molecular weights of ~14,000 g/mol enter live cells quickly, within 10 minutes upon incubation, through the cancer cell membrane.

Conventional methods of synthesizing CPs with diverse functional group are tedious and problematic. In addition to intrinsic synthetic challenges of optimizing polymerization conditions for each monomer, the resulting CP with different functional groups will have different molecular weight and polydispersity, which will influence their physical and biophysical behaviors. It is therefore desirable to form a nanoparticle or a CP that has attached modified guanidine moieties. These may provide rapid and tailored cellular delivery of anti-MDR siRNA for dramatically enhanced chemotherapy efficiencies that can impact cancer treatment.

Cell membranes are impermeable to most macromolecules. Many drug candidates fail to advance clinically because they do not have the properties needed to cross biological membranes and reach their intracellular target. Additionally, poor pharmacokinetics, stability, and off-target effects lead to undesirable biological responses. Thus, there is a need to develop novel delivery materials that overcome the biological barrier.

BRIEF SUMMARY

The subject invention provides materials and methods for disrupting the mucus layer and intracellularly delivering therapeutic agents such as drugs, nucleic acids and proteins. The subject invention also provides methods for design and synthesis of nanomaterials that enhance or assist the passage of therapeutic agents across biological membranes.

In one embodiment, the subject invention provides nanomaterials as molecule transporters for targeted delivery of therapeutic agents into cells, preferably, cancer cells for inhibiting the growth of cancer cells and altering gene expression in these cells.

In one embodiment, the nanomaterial of the subject invention comprises a modulated guanidine substituted polymer or nanoparticle, the modulated guanidine substituted polymer or nanoparticle comprising a guanidine moiety on a plurality of repeating units of a polymer, or on the surface of a nanoparticle, the modulation comprising a substituted amidinourea or amidinocarbamate or salt thereof. Preferably, the modulation comprises the substituted amidinourea or salt thereof.

In one embodiment, the substituted amidinourea or salt thereof comprises a hydrophobic modulation, wherein the hydrophobic modulation can be, for example, an N-alkylamino; N-arylamino; N-(alkylaryl)amino; N-(aryalkyl) amino; N, N-dialkylamino; N, N-diarylamino; N, N-di(alkylaryl)amino; N, N-di(aryalkylamino); N-alkyl, N-arylamino; N-alkyl, N-(alkylaryl)amino; N-alkyl, N-(aryalkyl)amino; N-aryl, N-(alkylaryl)amino; or N-aryl, N-(arylalkyl)amino group.

In a further embodiment, the alkyl group is a C2 to C22 straight, branched, cycloalkyl or alkyl substituted cycloalkyl group, and the aryl group is a C6 to C22 mono- or polycyclic aromatic group.

In one embodiment, the hydrophobic modulation comprises a heterocyclic modulation, wherein the heterocyclic modulation comprises an unsubstituted or substituted morpholine, pyrolidine, pyrrole, piperidine, ethyleneimine, indole, isoindole, or carbazole.

In one embodiment, the substituted amidinourea or salt thereof comprises a hydrophilic modulation, wherein the hydrophilic modulation can be, for example, imidazole, purine, aminoethanol, or amino terminal polyethylene oxide.

In one embodiment, the modulated guanidine substituted polymer or nanoparticle comprises a guanidine moiety on a plurality of repeating units of a polymer, or on the surface of a nanoparticle, the modulation comprises a substituted or unsubstituted amidinocarbamate or salt thereof. Preferably, the amidinocarbamate or salt thereof comprises a substituted or unsubstituted alky carbamate, aryl carbamate, alkylaryl carbamate or aryalkyl carbamante.

In one embodiment, the modulated guanidine substituted polymer comprises a conjugated polymer. The conjugated polymer comprises, for example, poly(phenyleneethynylene), poly(phenylenevinylene), poly(phenylene), poly (fluoreine), polythiophene, or any p-electron conjugated polymer. Preferably, the conjugated polymer comprises a polymer chain/structure according to the subject invention.

The polymer of the modulated guanidine substituted polymer can be a natural or synthetic polymer.

In one embodiment, the nanoparticle comprises silica, alumina, titania, zinc oxide, tin oxide, silver oxide, cuprous oxide, cupric oxide, ceria, vanadium oxide zirconia, molybdenum, tungsten oxide, barium oxide, calcium oxide, iron oxide, or nickel oxide.

In one embodiment, the subject invention provides a method of preparing a modulated guanidine substituted polymer or nanoparticle, the method comprising:

providing a N-Boc protected guanidine substituted polymer or N-Boc protected guanidine substituted nanoparticle and a solvent to form a solution or suspension;

adding an amine or an alcohol to the solution or suspension to make a reaction solution or suspension;

heating the solution or suspension to a temperature of at least 80° C.; and isolating the modulated guanidine substituted conjugated polymer or nanoparticle or a suspension or solution thereof.

In one embodiment, the subject invention provides methods for treating cancer using the modulated guanidine substituted polymer or nanoparticle according to the subject invention. The cancer treatment, comprising:

providing a modulated guanidine substituted polymer or nanoparticle of the subject invention;

combining the modulated guanidine substituted polymer or nanoparticle with a vehicle and, optionally, adjuvants to deliver the modulated guanidine substituted conjugated polymer or nanoparticle to form a therapeutic formulation;

delivering the therapeutic formulation to a cancer patient.

DETAILED DISCLOSURE

Figure 1:
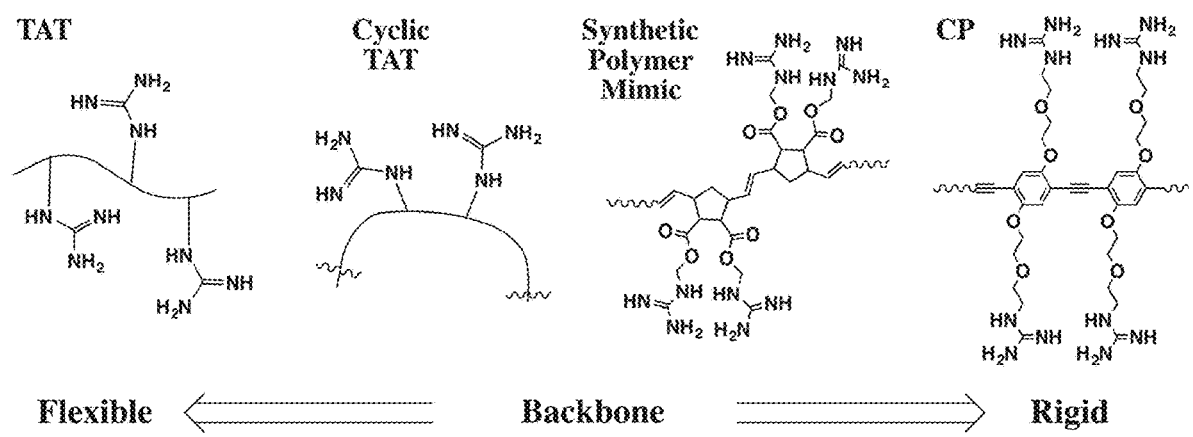
FIG. 1 shows a schematic comparison of flexible tyrosine aminotransferase (TAT) synthetic mimics vs the backbone rigidity of the guanidine comprising conjugated polymer, (G-CP).

The subject invention provides materials and methods for disrupting the mucus layer and intracellularly delivering therapeutic agents such as drugs, nucleic acids, peptides, and proteins. The subject invention also provides methods for the design and synthesis of polymeric systems and nanomaterials that enhance or assist the passage of therapeutic agents across biological membranes.

In one embodiment, the subject invention provides polymeric systems comprising cell-penetrating peptide (CPP)-like moieties for transporting therapeutic agents and/or biological molecules across biological membranes. The polymeric systems can be used as molecular transporters that facilitate the internalization of therapeutic agents and/or biological molecules by cells. Advantageously, the properties of the polymeric systems can be tuned by modulating the chemistry and architecture of the materials. Specifically, by retaining only the key features of CPPs necessary for sufficient internalization and delivery of the cargo, CPP synthetic mimics (CPPMs) have improved properties compared to naturally-occurring CPPs.

In one embodiment, the subject invention provides molecular transporters for intracellularly delivering therapeutic agents such as drugs, nucleic acids, peptides and proteins.

In one embodiment, the molecular transporter comprises a modulated guanidine substituted polymer or nanoparticle, the modulated guanidine substituted polymer or nanoparticle comprising a guanidine moiety on a plurality of repeating units of a polymer, or on the surface of a nanoparticle, the modulation comprising a substituted amidinourea or amidinocarbamate or salt thereof. Preferably, the modulation comprises the substituted amidinourea or salt thereof.

In one embodiment, the molecular transporters of the subject invention can be synthesized using ring-opening metathesis polymerization (ROMP). ROMP has great benefits over other polymerization techniques, which include controlled polymer length, low polydispersity index (PDI) and easy copolymer design.

In one embodiment, the polymer is a conjugated polymer (CP). Biodegradable CPs can be formed by introducing flexible degradable functional groups along the backbone of the CP that can be used for quantitative labeling of mitochondria. Cellular interaction and internalization of CPs are dependent on the chemical structures of both the backbone and side chains of the CPs. CPs with guanidine units (G-CPs), as disclosed in Moon et al. U.S. Pat. Nos. 9,676,886 and 9,757,410, and incorporated herein by reference, that have molecular weights of ~14,000 g/mol, enter live cells quickly through the cancer cell membrane. After generating positive charges on guanidine, the resulting polymers are soluble in DMSO, and form nanoparticles in PBS buffer with a hydrodynamic diameter of about 56 nm. Live cells treated with CPs containing various functional groups display surface morphologies at the submicron level that are dependent on the chemical functionalities of the CPs.

Figures 2A, 2B:
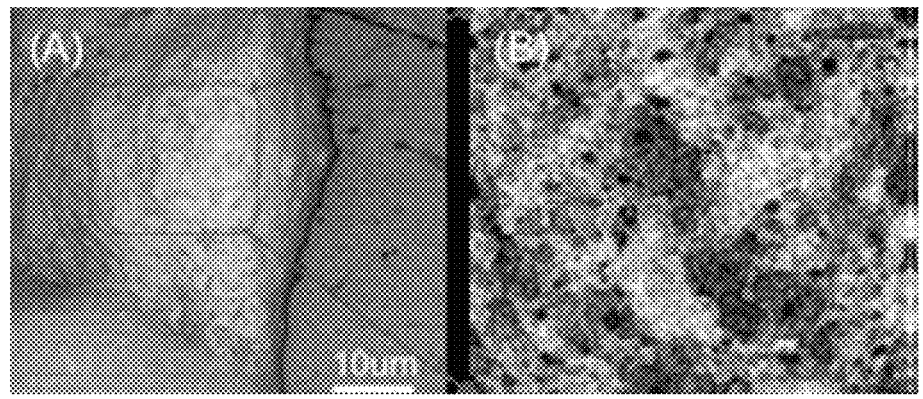
FIG. 2A shows a scanning ion-conductance microscopy (SICM) image of HeLa cells treated with G-CP.
FIG. 2B shows a magnified image where the pore formation on the surface of the HeLa cells has been induced by the G-CP.
Figure 2C:
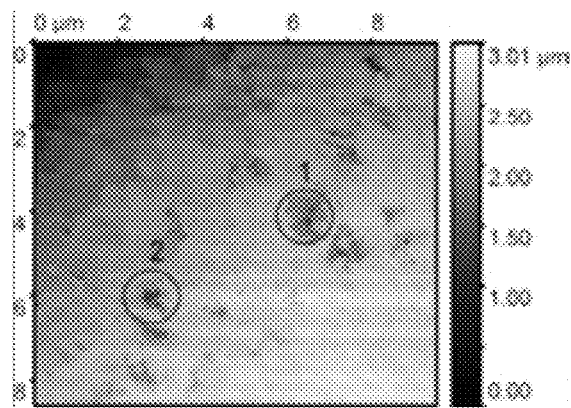
FIG. 2C shows a SICM topographic image of the HeLa cells treated with G-CP and labeled with m-Cherry protein.
Figure 2D:
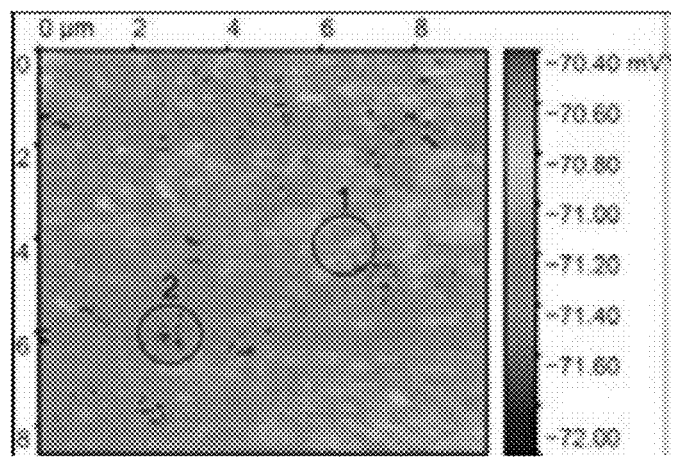
FIG. 2D shows a SICM potential map of the same area as FIG. 2C showing the presence of numerous pores.
Figure 2E:
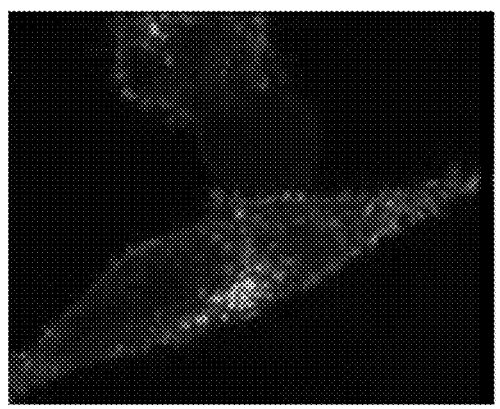
FIG. 2E shows a confocal microscopic image of HeLa cells incubated with fluorescing G-CP for 10 min supporting fast cellular entry of G-CP.

As can be seen in FIGS. 2A and 2B, the scanning ion conductance microscopy images indicate pores on the cells surface. The potential at the pores are lower than for the rest of the area, suggesting formation of pore-like features on the membrane (FIGS. 2C and 2D). Based on the different potentials at the topographic pores, different stages of cellular entry of CP are suggested (FIG. 2E). Confocal microscopic imaging also supports fast and efficient cellular entry of G-CP. Within 10 min, a significant amount of G-CP was found in the intracellular compartments.

Ideal small interfering RNA (siRNA) delivery requires RNA protection, excellent pharmacokinetics, targeting, cellular entry, and release of siRNA in the cytosol of target cells. The biophysical properties of positively charged carriers complexed with negatively charged siRNA can be tailored by introducing functional groups at the positive charge. Positively charged carriers often exhibit toxic effects and promote high blood clearance through opsonization, limiting clinical applications.

According to one embodiment of the invention, on-ionic group, including, but not limited to, hydrophobic lipids and hydrophilic PEGs, at the positive charge improve carriers' biophysical properties, provided that the modification does not diminish the ionic complexation and cellular entry. Unlike modulated guanidine on TAT peptides, which decreases entry efficiency, G-CPs modulated with various functional groups exhibit enhanced biophysical properties.

Figure 3:
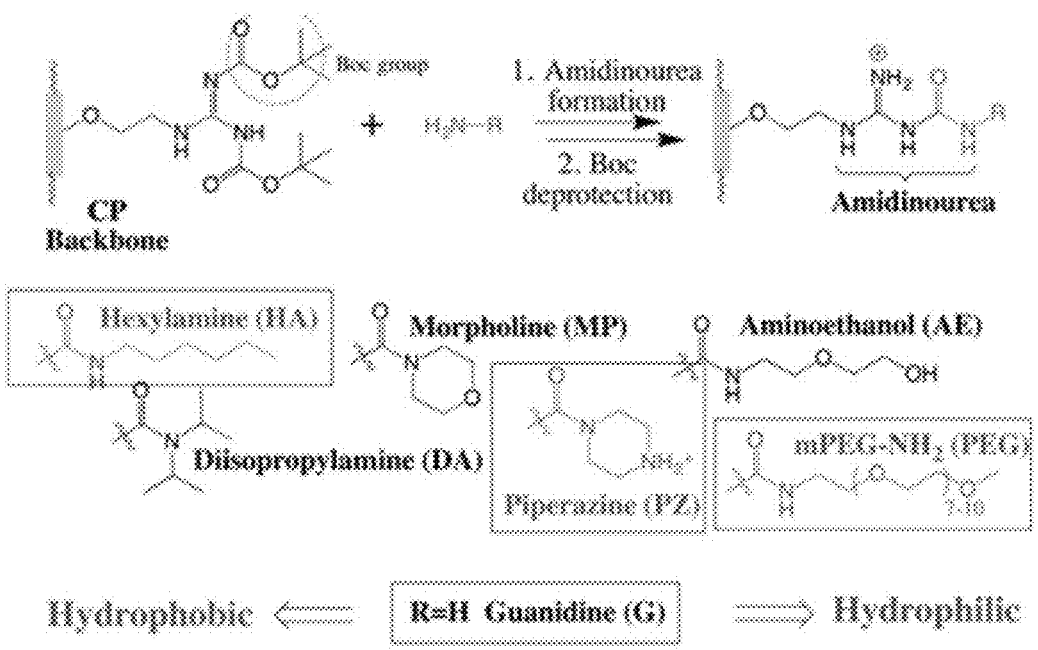
FIG. 3 shows a scheme for the modulation of the chemical environment at the guanidine group by amidinourea formation, according to an embodiment of the invention.
Figure 4A:
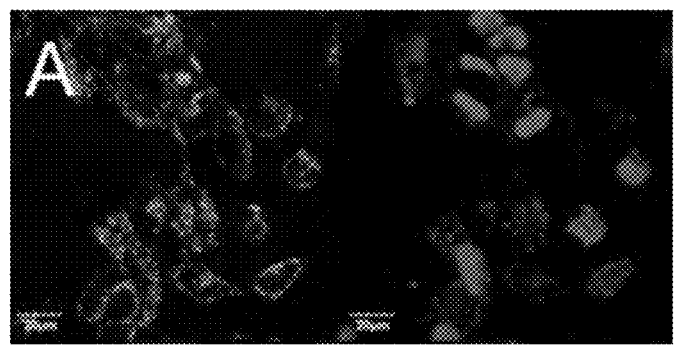
FIG. 4A show a fluorescent microscopic images of HeLa cells incubated with modulated guanidine complex for 1 h where the modulating amine was aminoethoxyethanol to form a hydrophilic G-CP, Poly-2, according to an embodiment of the invention, with CP shown in the left panel and siGLO on the right panel.
Figure 4B:
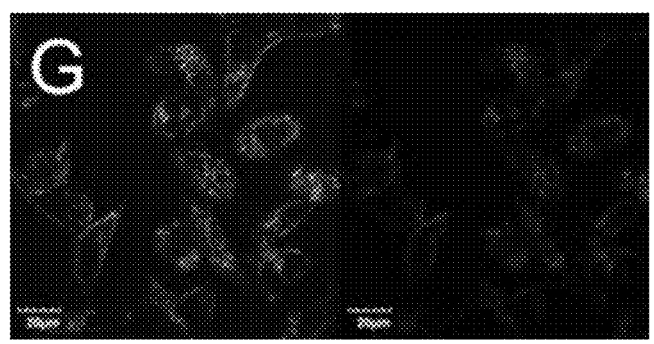
FIG. 4B show a fluorescent microscopic images of HeLa cells incubated with guanidine complex for 1 h to form a G-CP, Poly-2, with CP shown in the left panel and siGLO on the right panel.
Figure 4C:
FIG. 4C show a fluorescent microscopic images of HeLa cells incubated with modulated guanidine complex for 1 h where the modulating amine was morpholine to form a slightly hydrophobic G-CP, according to an embodiment of the invention, with CP shown in the left panel and siGLO on the right panel.
Figure 4D:
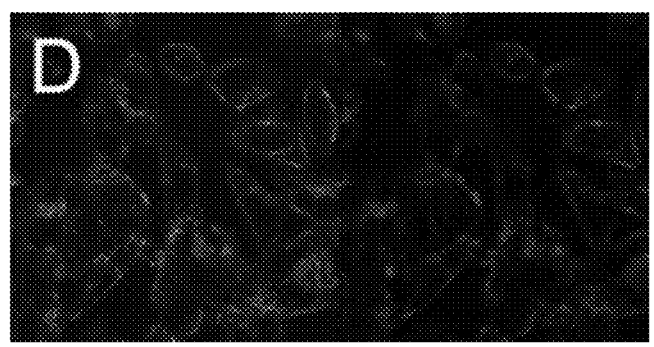
FIG. 4D show a fluorescent microscopic images of HeLa cells incubated with modulated guanidine complex for 1 h where the modulating amine was diisopropylamine to form a hydrophobic G-CP, according to an embodiment of the invention, with CP shown in the left panel and siGLO on the right panel.

Modulated G-CPs, according to one embodiment of the invention, as shown in FIG. 3, have an aminoethoxyethanol groups at the positive charge of the guanidines to increase the efficiency of cellular entry and siRNA delivery, as illustrated in FIG. 4A vs FIG. 4B for guanidines, while exhibiting no viability inhibition. Addition of a morpholine group at the charged guanidine changed the cellular entry behaviors dramatically, as shown in FIG. 4C, as indicated by the diffused uniform staining of the cytosol. Addition of a bulky diisopropylamine group at the charged guanidine appears to diminish the cellular entry behavior, as shown in FIG. 4D.

Modulating the charged group with specialized functional groups, such as, but not limited to, tumor cell surface targeting ligands, PEG, or drugs, can offer tailored cellular targeting and entry to achieve optimized therapeutic efficacy. Because the drug and gene knockdown efficacy is highly unique on each tumor due to the unique tumor microenvironment, no generalized carrier will work equally on each tumor. Modulation, as indicated above, allows facile optimization for a tumor because of the straightforward chemical modulation chemistry that can be carried out. Any commercially available amine or alcohol, which can be readily transformed to an amine, or alcohol can be directly coupled to guanidine via the Mitsnobu reaction, can be added to the positively charged guanidine group. Using this synthetic approach to modulate G-CPs, a library of potential agents for screening and ultimate use against specific tumor types can be tailored for cellular entry and efficacy. Because the conventional and frequently used tumor cell lines have significantly different cellular features from patient tumors, drug delivery systems developed and optimized using the conventional cell lines can have large discrepancies in therapeutic efficacy when drugs are administered to patients.

Modulating the chemical environments at the positively charged guanidine functional group of the CP is used to optimize siRNA delivery. Embodiments of the invention are directed to a method to form CPs where there is introduced various functional groups of hydrophilic or hydrophobic molecules at the guanidine group, as can be seen in FIG. 3 of such CPs. The modulated CPs exhibit enhanced cellular entry, modulated intracellular localization, and better siRNA delivery. The modulated CPs promote: enhanced siRNA delivery by G-CP modulated with functional groups including short ethylene glycol (EG); efficient knockdown of MDR associated genes; and increased drug potency over cancer cells. The fine-tuning allows better protection, cellular entry, and release of siRNA. Less siRNA can be used for controlling the gene expression levels.

The conjugated polymers (CPs), according to embodiments of the invention, are macromolecules with highly delocalized π-conjugated backbones and amphiphilic side chains. CPs display large absorption extinction coefficients, amplified quenching, high quantum yields, and tunable absorption and emission maxima. Guanidine is a part of the side chain of arginine and remains charged over a wide pH range, which is reflected in the high pKa value (12.48) of its protonated counterpart. There are a great number of guanidine moieties peptides available due to their ease of modification and straight-forward synthetic strategy. Guanidinum groups provide the CPs with cationic properties and act as mimics of cell-penetrating peptides (CPPs), molecular recognition, and antimicrobial agent.

Chemical modulation at the positive charge of a guanidinium-containing modulated CP is shown to efficiently knockdown a target gene of well-differentiated primary human bronchial epithelium cells, which closely mimic many in vivo phenotypes of airway epithelium including: regulation of ion transport; mucous secretion; and mucociliary clearance. Not to be bound by a mechanism, the positive charges needed for ionic complexation of siRNA appear to increase adsorption to a mucus layer, resulting in decreased transfection efficiency and higher blood clearance by absorbing various serum proteins. In embodiments of the invention, amidinourea formation introduces hydrophilic PEG-like functional groups at the positive charge by reacting Boc-protected guanylurea to address these shortcomings.

Figure 5:
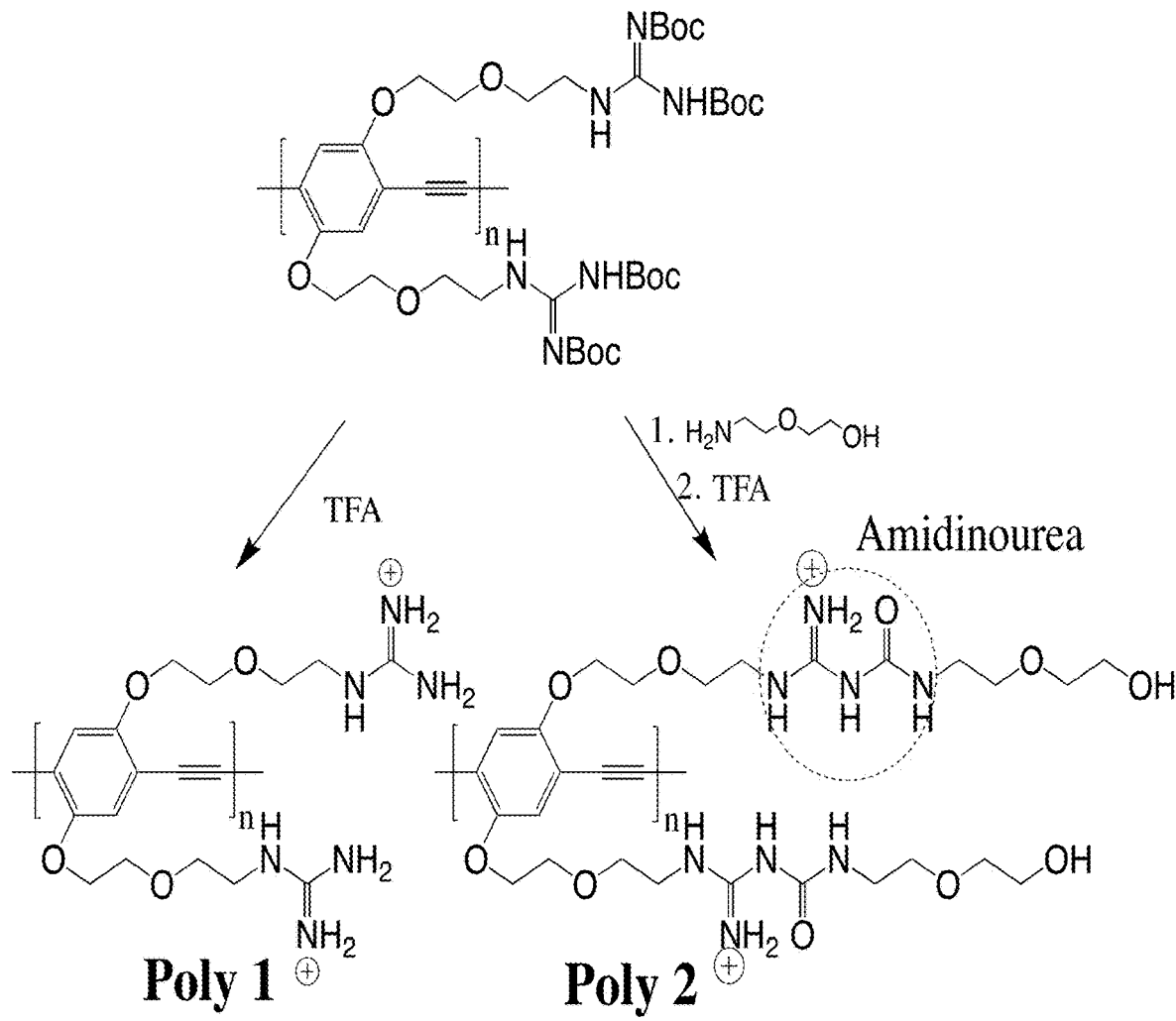
FIG. 5 is a reaction scheme for the preparation of Poly-1 and Poly-2 of a G-CP, according to an embodiment of the invention.
Figure 6A:
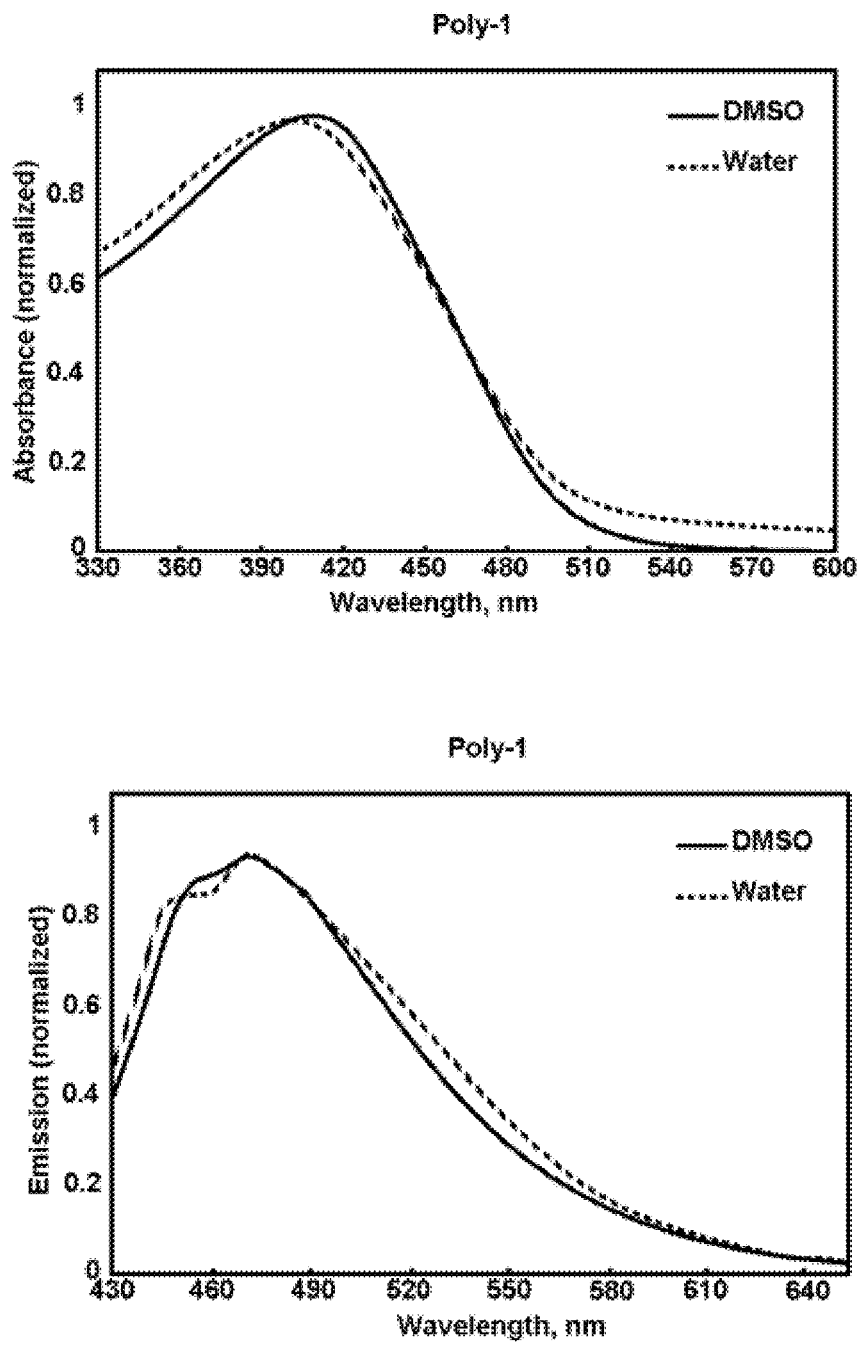
FIG. 6A shows UV absorbance (left) and emission (right) spectra of Poly-1 in DMSO and 95% water/5% DMSO.
Figure 6B:
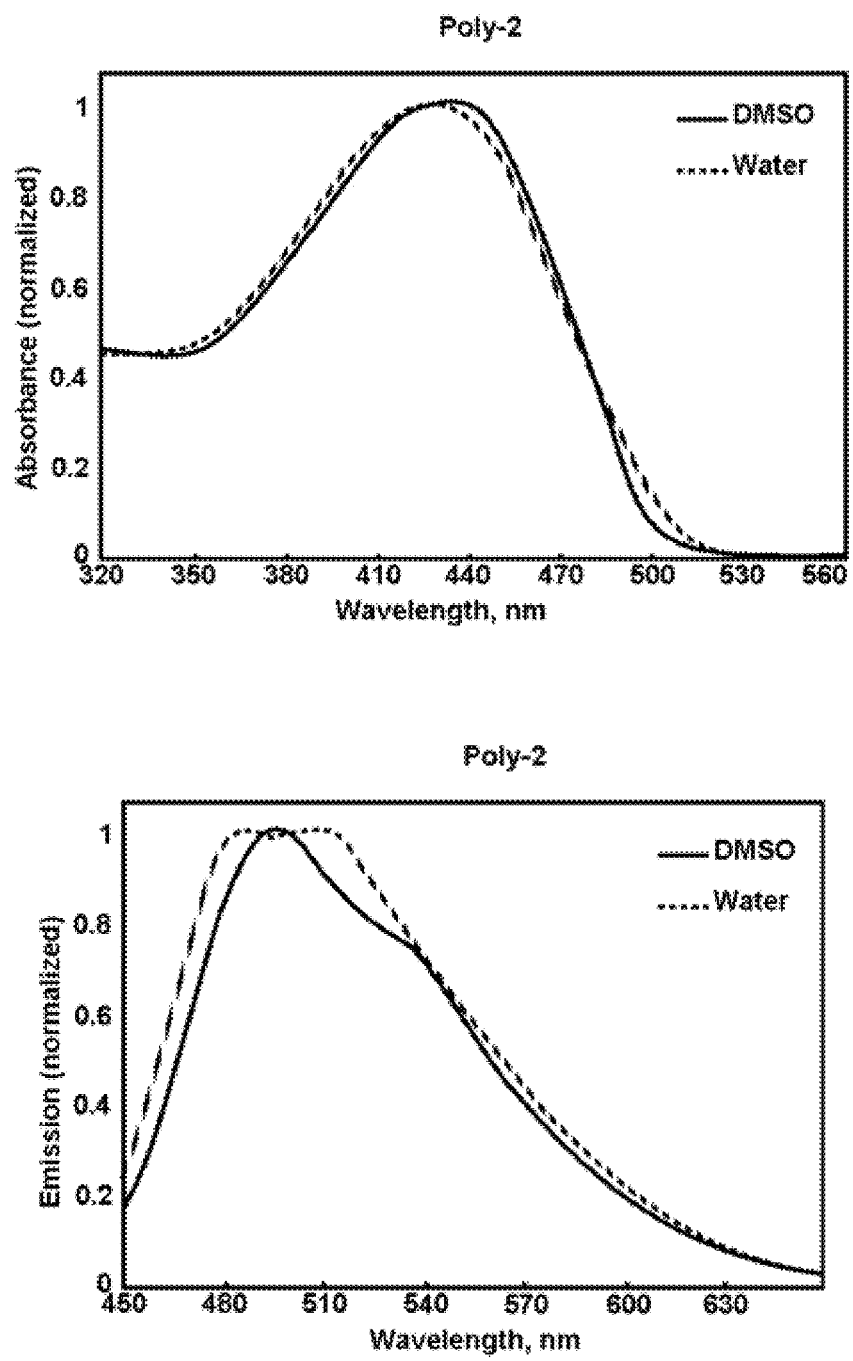
FIG. 6B shows UV absorbance (left) and emission (right) spectra of Poly-2 in DMSO and 95% water/5% DMSO.
Figure 7A:
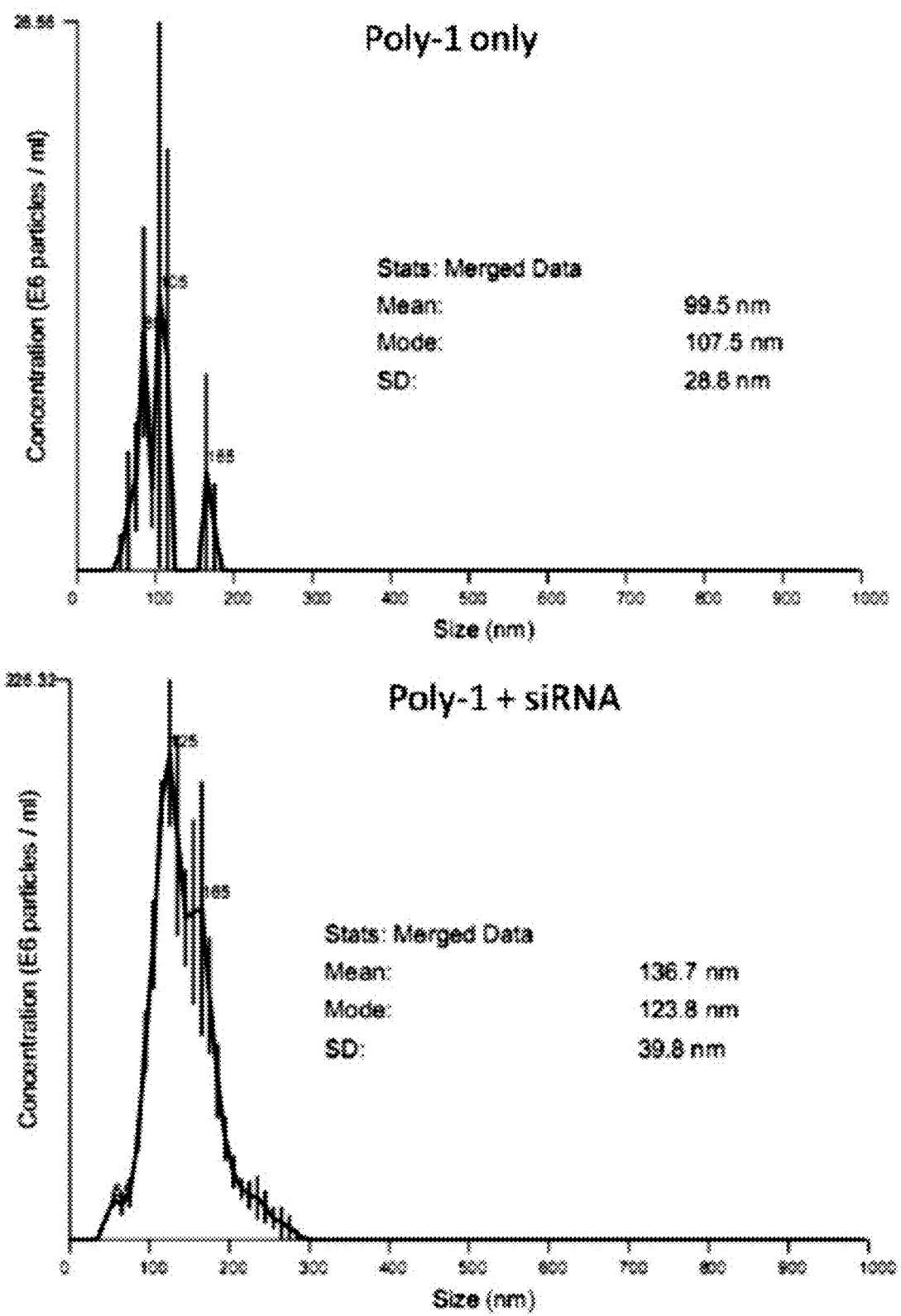
FIG. 7A shows a nanoparticle tracking analysis (NTA) of Poly-1.
Figure 7B:
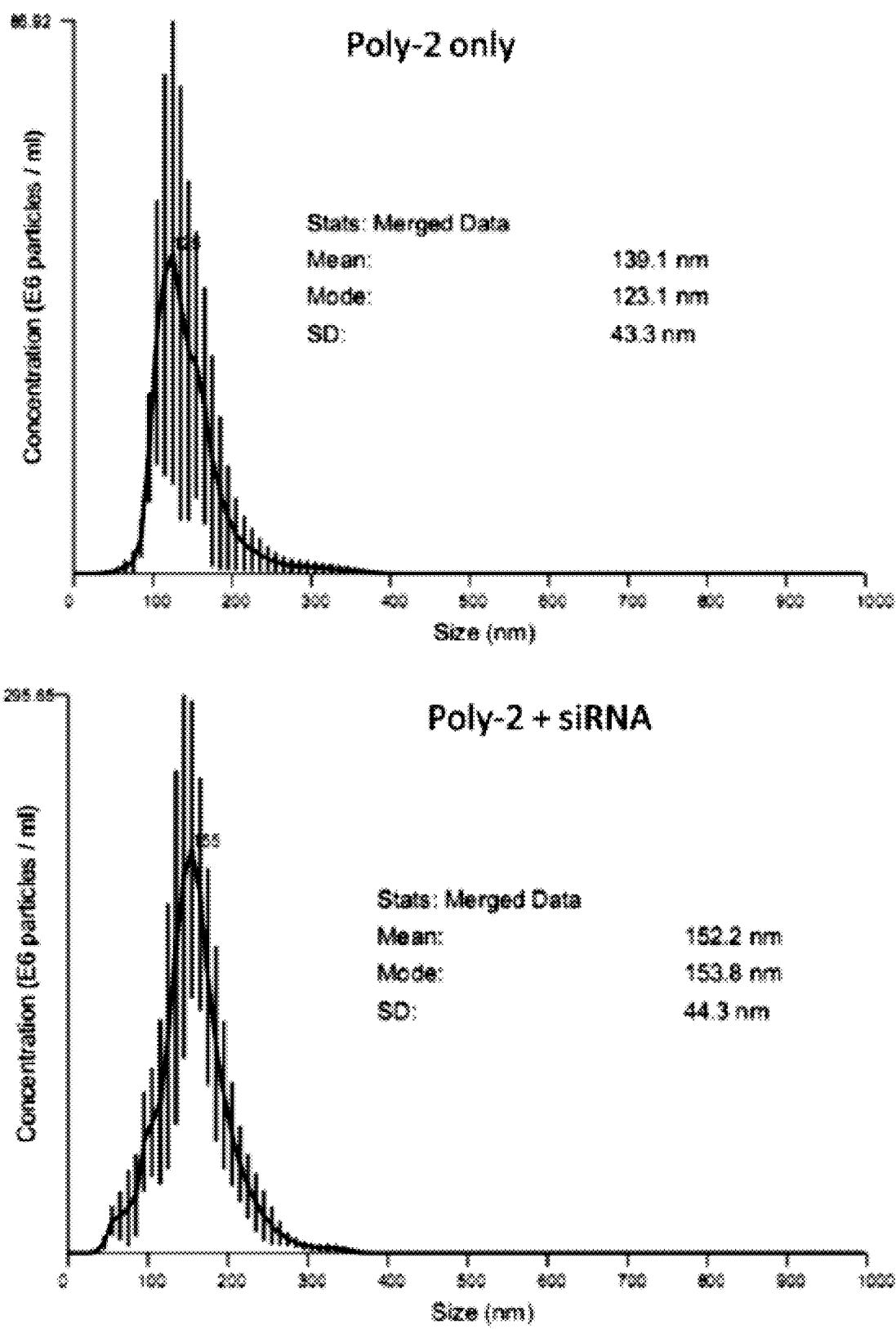
FIG. 7B shows a NTA of Poly-2.
Figure 8A:
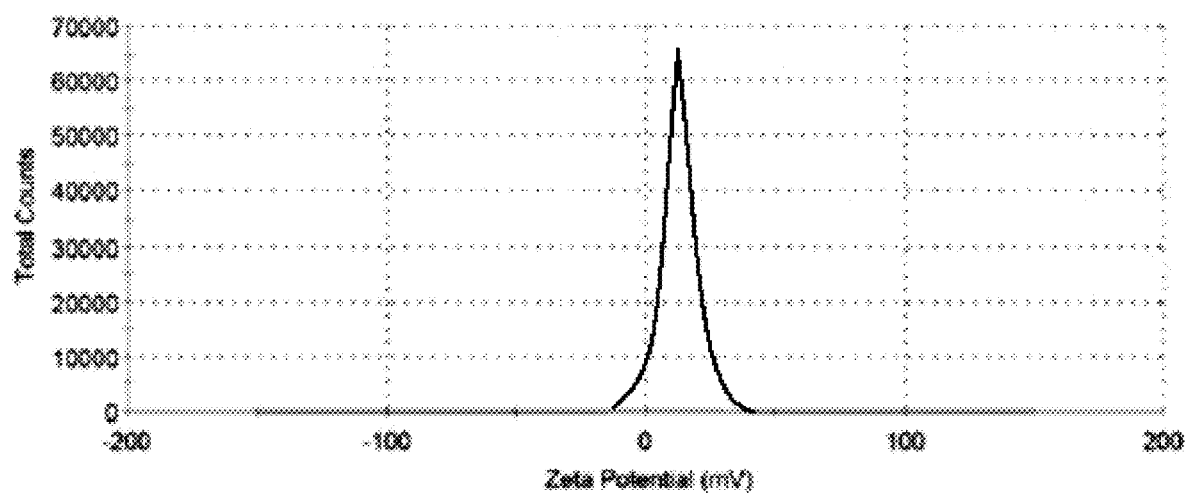
FIG. 8A shows a plot of zeta potential for Poly-1 with siRNA.
Figure 8B:
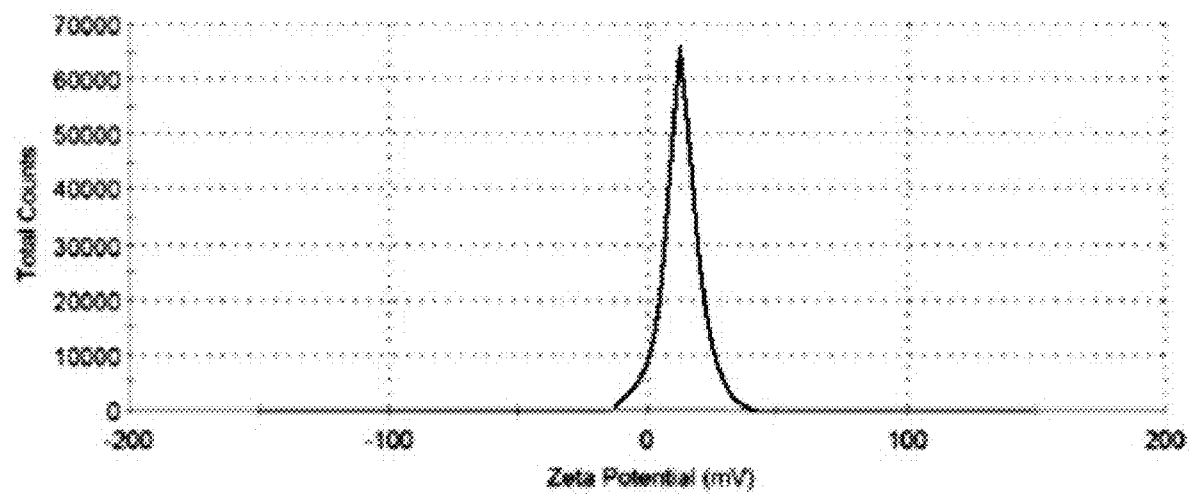
FIG. 8B shows a plot of zeta potential for Poly-2 with siRNA.

Hydrophilic PEG-like functional groups are introduced at the positive charge by reacting Boc-protected guanidine with aminoethoxyethanol followed by Boc deprotection as shown in FIG. 5. According to an embodiment of the invention, Poly-2 of FIG. 5 is successfully synthesized in high yields, with formation of a guanylurea group in every repeating unit, as characterized by an amide proton signal in $^{1}$H-NMR spectra at about 12.3 ppm. Poly-2 exhibits good solubility in common organic solvents, characteristic absorption/emission profiles of CPs, as shown in FIGS. 6A and 6B, and has about a three-fold greater fluorescent quantum yield than Poly-1. Poly-1 and Poly-2 exhibit very weak dynamic light scattering signals even at concentrations in excess of the mM levels, implying that the non-aqueous soluble CPs are relatively well-solvated due to the highly charged guanidine and guanylurea, preventing hydrophobic backbone aggregation. Upon complexation of the CPs with the negatively charged siRNA, nanometer-sized polymer/siRNA polyplexes are formed. The hydrodynamic diameters (HDs) of Poly-1 and 2 are 137±40 and 152±44 nm, respectively, as shown in FIGS. 7A and 7B. Zeta potentials of both polyplexes are slightly positively charged, about +13 mV, as shown in FIGS. 8A and 8B.

Figure 9:
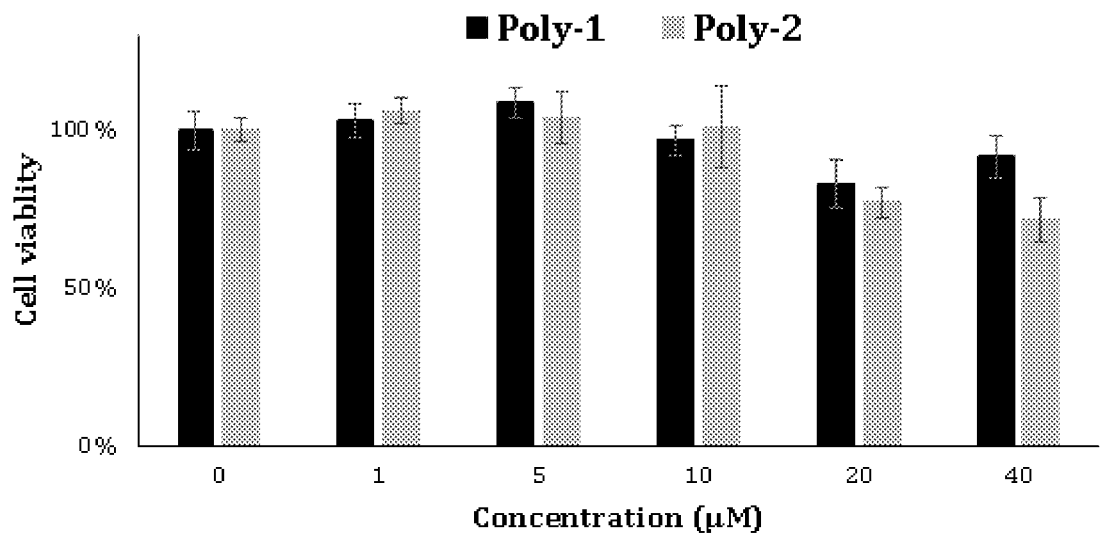
FIG. 9 shows a bar chart for Cell viability inhibition by Poly-1 and Poly-2.
Figure 10:
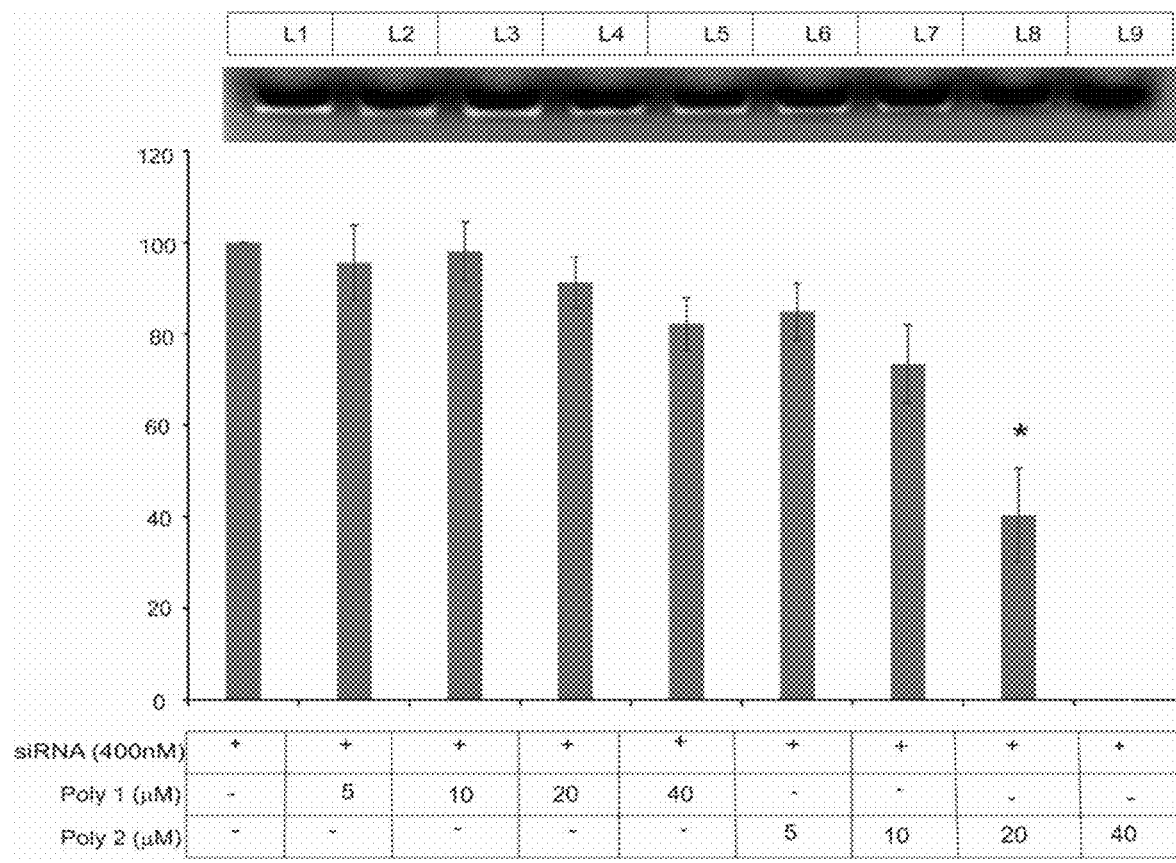
FIG. 10 shows a polyacrylamide gel electrophoresis retardation assay, top, where Lane 1: siRNA (400 nM); Lane 2: siRNA (400 nM)+Poly 1 (5 µM); Lane 3: siRNA (400 nM)+Poly 1 (10 µM); Lane 4: siRNA (400 nM)+Poly 1 (20 µM); Lane 5: siRNA (400 nM)+Poly 1 (40 µM); Lane 6: siRNA (400 nM)+Poly 1 (5 µM); Lane 7: siRNA (400 nM)+Poly 1 (10 µM); Lane 8: siRNA (400 nM)+Poly 2 (20 µM); and Lane 9: siRNA (400 nM)+Poly 2 (40 µM), where significance at $p<0.05$.

No cell viability inhibition was exhibited at up to 4004 concentration of either Poly-1 or Poly-2, demonstrating that supporting the modulation at guanidine does not raise viability inhibition. As indicated in FIG. 9, the siRNA against histone deacethylase (HDAC) (siHDAC) was delivered by both Poly-1 and Poly-2 to BEAS-2B cell lines, where mRNA expression levels are quantified by RT-qPCR using glyceraldehye 3-phosphate dehydrogenase (GAPDH) as a control gene. By Gel retardation assay, as shown in FIG. 10, the guanylurea-functionalized Poly-2 exhibits much better siRNA complexation than the guanidine-containing Poly-1. The entire siRNA is complexed by Poly-2 at an N (nitrogen)/P (phosphate) ratio of about 5, whereas Poly-1 showed only complexes about 20% at that ratio.

Figure 11A:
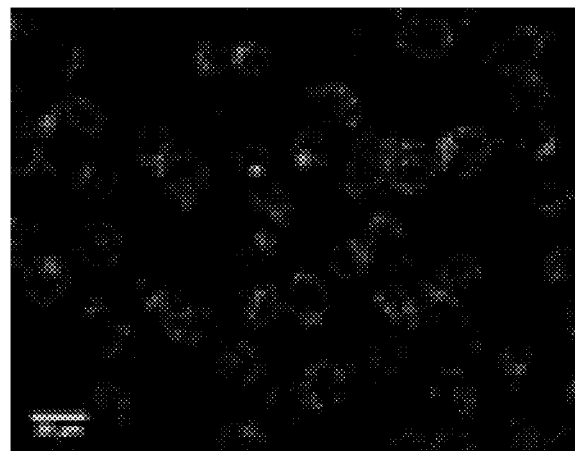
FIG. 11A shows a confocal microscopic image of BEAS-2B cells incubated with CP/siGLO polyplexes for 1 h show CP-mediated siRNA delivery for Poly-1 located in the cytosol having a green signal from the CP.
Figure 11B:
FIG. 11B shows a confocal microscopic image of BEAS-2B cells incubated with CP/siGLO polyplexes of Poly-1 for 1 h where a red signals from siGLO is observed.
Figure 11C:
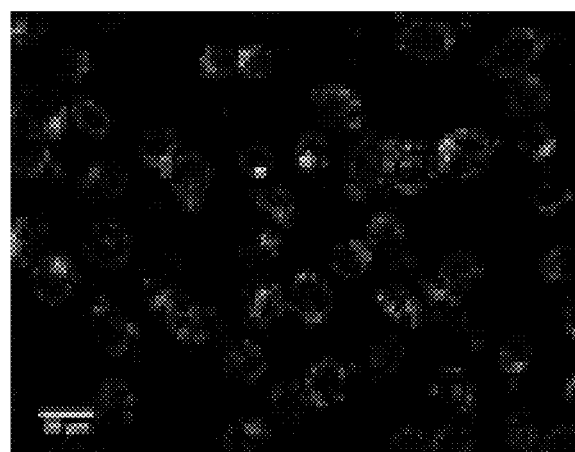
FIG. 11C shows a combined signal from the CP and siGLO in from cells treated with Poly-1 in a confocal microscopic image of BEAS-2B cells incubated with CP/siGLO polyplexes of Poly-1 for 1 h.
Figure 11D:
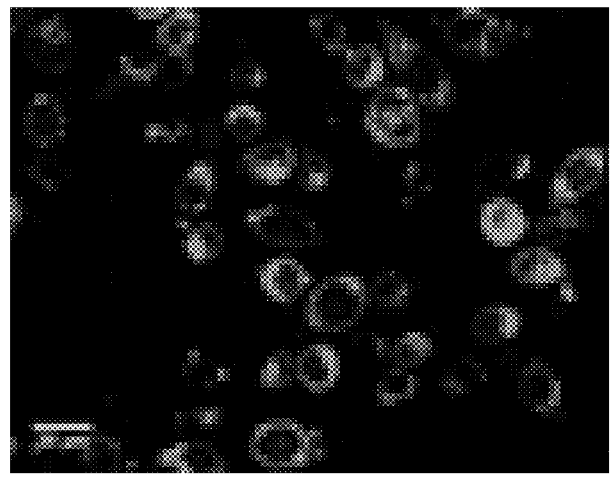
FIG. 11D shows a confocal microscopic image of BEAS-2B cells incubated with CP/siGLO polyplexes for 1 h show CP-mediated siRNA delivery for Poly-2 located in the cytosol having a green signal from the CP.
Figure 11E:
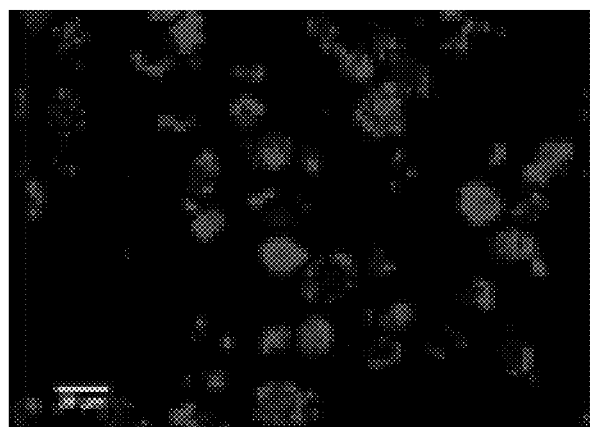
FIG. 11E shows a confocal microscopic image of BEAS-2B cells incubated with CP/siGLO polyplexes of Poly-1 for 1 h where a red signals from siGLO is observed.
Figure 11F:
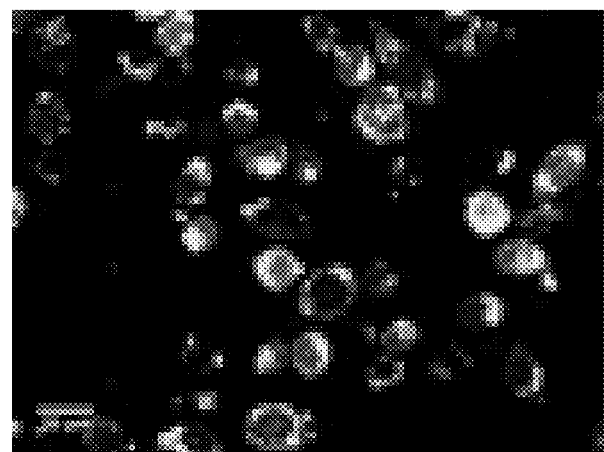
FIG. 11F shows a combined signal from the CP and siGLO in from cells treated with Poly-2 in a confocal microscopic image of BEAS-2B cells incubated with CP/siGLO polyplexes of Poly-1 for 1 h where a portion of siGLO were released from Poly 2 and localized in the nucleus.

Using a fluorescently labeled control siRNA (i.e., siGLO Red), CP-mediated siRNA delivery for Poly-1 and Poly-2 is confirmed by confocal microscopy, as shown in FIGS. 11A, 11B, and 11C and FIGS. 11D, 11E, and 11F, respectively. After an hour of incubation at the N/P ratio of about 9, the CPs and siGLO reside inside BEAS-2B cells. The relatively high amount of siGLO observed in cells incubated with Poly-2, indicates that guanylurea modification increases siRNA delivery efficiency. The strong siGLO complexation by Poly-2, results in higher amounts of intracellular siGLO due to enhanced cellular entry of the complex resulting from a balance of hydrophobicity and charge density. When the positive charge of guanidine is balanced with hydrophobic moieties, polymers with many guanidine-containing carriers exhibit efficient membrane interaction followed by high intracellular entry. A portion of siGLO is found in the nuclei of cells treated with Poly-2/siGLO, as indicated in FIGS. 11E and 11F; indicating siGLO is released from Poly-2. From this result, it appears that hydrophilic modification at the positive charge of CPs allows better siRNA complexation, efficient cellular entry, and subsequent intracellular release of siRNA.

The guanylurea-functionalized CP for delivery of siRNA, according to an embodiment of the invention, was evaluated in a physiological setting, where ex vivo primary bronchial epithelial cells were incubated with Poly-2/siGLO polyplex. Primary bronchial epithelial cells obtained from nasal turbinates or cadaver lungs were grown in plastic dishes or on porous supports at the air-liquid interface. While the cells grown on plastic dishes present a poorly differentiated squamous phenotype, the cells grown on porous supports at the air-liquid interface closely recapitulate their normal in vivo morphology, including: the cell-matrix and cell-cell interactions; differentiation of mucus, goblet, and ciliary cells; polarized epithelial ion transport; and regenerating the native bronchial epithelium ex vivo. Therefore, ex vivo primary human bronchial epithelial cells are an excellent model of the constituted airway epithelial and are used for ex vivo drug delivery studies before extrapolating to large animal models or human clinical studies.

Figure 12:
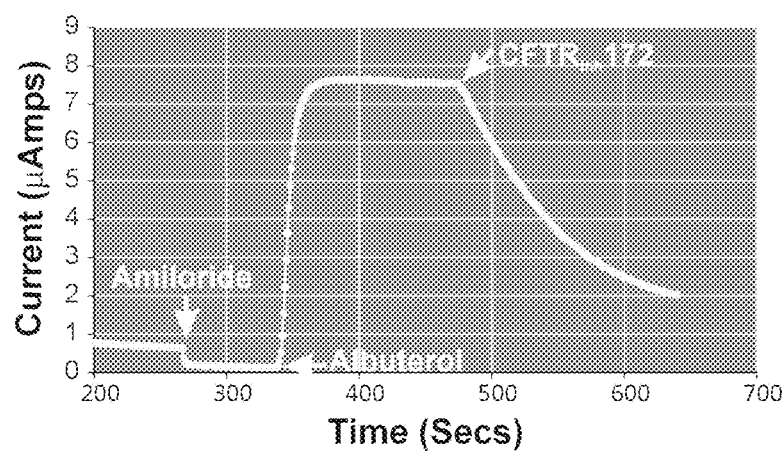
FIG. 12 shows a plot of polarization upon addition of a CFTR activator (albuterol to block the epithelial sodium channel) followed by an inhibitor ($CFTR_{inh}172$) to NHBE cells mounted in a Ussing chamber where a large apical current change with the cultured NHBE cells exhibiting the characteristic membrane polarization of epithelium.

Conformation of the polarity and integrity of the epithelium carried out by trans-epithelial electrical resistance (TEER) measured after 21 days of differentiation at the air-liquid interface, where primary NHBE cells exhibit a mean TEER value of 731 ohms/cm$^2$, indicating efficient barrier formation. The apical chloride ion flux, monitored by treatment with albuterol activates the cystic fibrosis trans-membrane conductance regulator (CFTR) protein to stimulate chloride ion flux. As shown in FIG. 12, a sharp current increase occurs immediately upon addition of albuterol. The specificity of CFTR-mediated efflux is indicated by the decreased current after addition of a CFTR inhibitor (i.e., CFIR$_{inh}$172).

Confocal microscopic images clearly indicate that Poly-2 delivers siGLO to NHBE cells, while cells treated with Poly-1/siGLO and Lipofectamine/siGLO, respectively, exhibited only background signals. The added hydrophilic groups near the positive charges promote diffusion of the ionic complex through the mucus layer followed by efficient intracellular entry.

Figure 13:
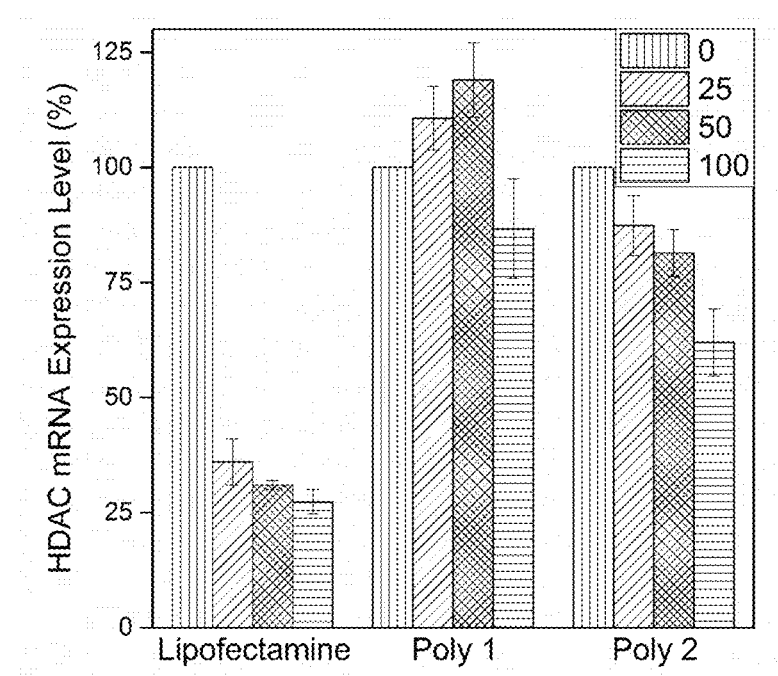
FIG. 13 is a bar chart of the HDAC mRNA knockdown efficiency in BEAS-2B cells for Lipofectamine, Poly-1 and Poly-2.
Figure 14:
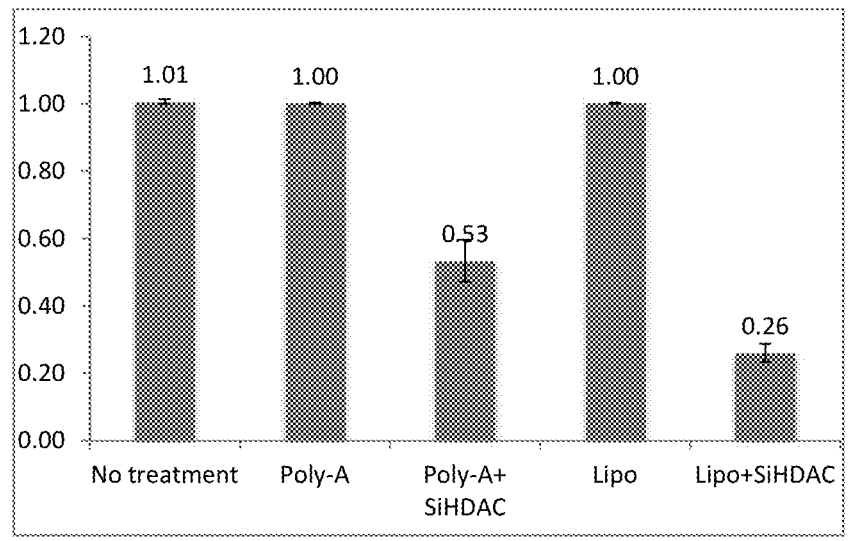
FIG. 14 is a bar chart of the relative knockdown efficiency of BEAS-2B cell treated with Poly-2/siHDAC, where Poly-A is Poly-2.
Figure 15:
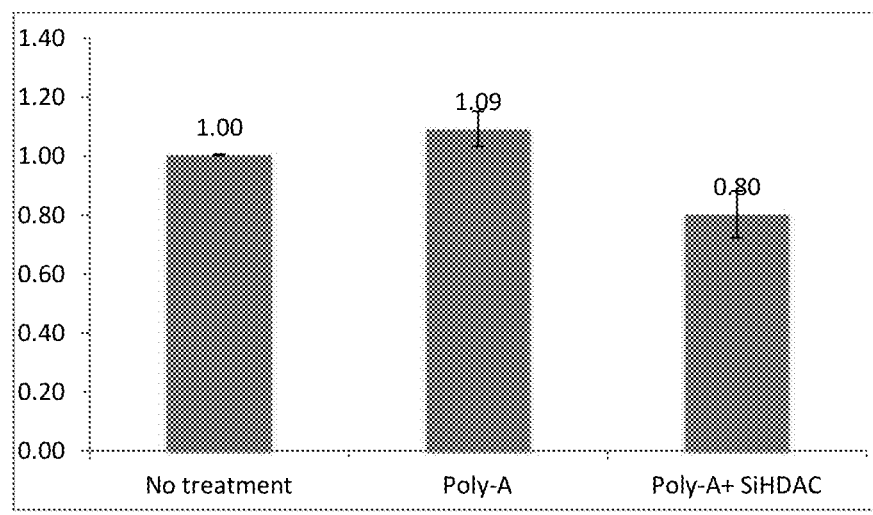
FIG. 15 is a bar chart of the relative HDAC mRNA expression level at primary NHBE cell treated with Poly2/siHDAC, where Poly-A is Poly-2.

The gene knockdown efficiency of Poly-2 was initially evaluated at the in vitro level using siRNA against histone deacethylase (HDAC) (siHDAC) in BEAS-2B cells. The mRNA expression levels were quantified by real time quantitative polymerase chain reaction (RT-qPCR) using glyceraldehyde 3-phosphate dehydrogenase (GAPDH) as a control gene. Inhibition of HDACs has been shown to suppress proliferation of non-small-cell lung cancer (NSCLC) and restore the drug sensitivity to NSCLC. The guanidine-modified Poly-1 exhibits relatively poor knockdown efficiency even in immortalized cell lines. Poly-2 and Lipofectamine exhibit a dose-dependent target gene knockdown, supporting that the guanylurea modification enhances RNAi efficiency, as indicated in FIG. 13. As FIG. 14 indicates, Poly-2 exhibit sufficient knockdown of the target gene at the mRNA level and is comparable to Lipofectamine. The HDAC mRNA expression level at primary NHBE cell treated with Poly-2/siHDAC indicates knockdown, as shown in FIG. 15, whereas Lipofectamine does not knock-down the target gene.

Figure 16:
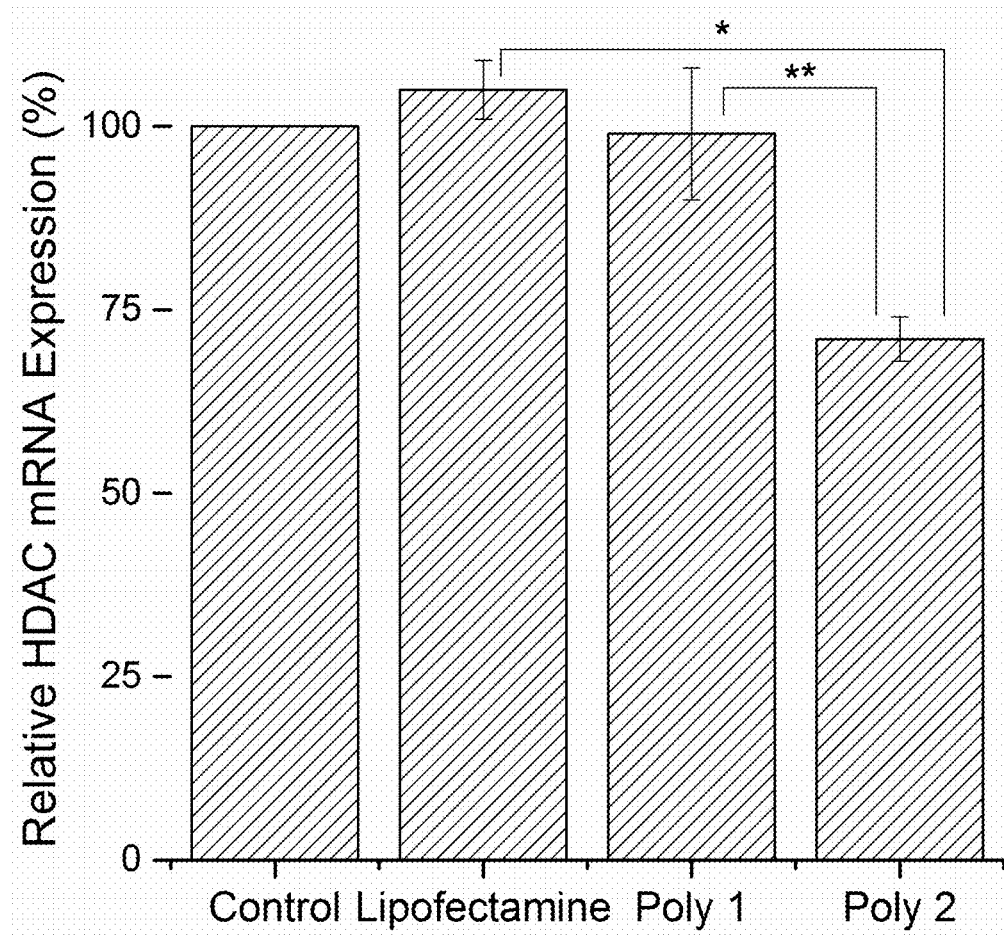
FIG. 16 is a bar chart of the relative HDAC mRNA expression levels of NHBE cells treated with Lipofectamine 2000 (a lipid-based), Poly 1 (cationic), and Poly 2 (with a modulated chemical environment at its positive charge), where $*p<0.0003$ and $**p<0.007$.

Both lipid-based and purely positively charged carriers, such as Poly-1, exhibit no or poor HDAC knockdown efficiency in well-differentiated NHBE cells, as shown in FIG. 16, due to poor cellular siRNA delivery to the epithelium cells. Meanwhile, Poly-2 consistently exhibits the average of about 30% knockdown efficiency over six independent lung samples. Due to the negatively charged hydrophobic mucus layers, positively charged Poly-1 and lipid-based carriers experience difficulty in diffusing through the mucus layer. The hydrophilic environment introduced at the positive charge of guanidine allows efficient ionic complexation and diffusion through the mucus layer.

Chemical modification of the guanidine group often destroys the function available for guanidine, where nitrogen atoms of guanidines, bearing electron-withdrawing substituents, act as a reactive nucleophile. Few methods for guanidine modification are known and they include the reaction between guanidine and alcohols under Mitsunobu reaction condition and alkylation of guanidine with electrophiles, such as alkyl halides, under basic conditions. Recently, Kessler et al. *Angew Chem Int Ed Engl.*, 2016, 55(4):1540-3 taught the modification of the guanidine group of Cilengitide ligand by N-methylation, N-alkylation, or N-acylation and successfully demonstrated an increasing selectivity of Cilengitide ligands. Takemoto et al. *J. Org. Chem.*, 2009, 74 (1), pp 305-11 taught the use of palladium- or iridium-catalysts and displayed a direct modification of guanidines. The direct modification of guanidine head group received much less attention and there are no reports of modification of guanidine moiety in polymer.

According to an embodiment of the invention, a catalyst free post polymerization reaction incorporates a variety of hydrophilic and hydrophobic functional groups onto conjugated polymers (CPs). By this method, structurally diverse polymers are synthesized without tedious polymerization steps. The modified polymers are easily analyzed using NMR spectroscopy and are prepared with high yields overall. The guanidine head group reacts with diisopropylamine (DIPA), which yields a CP with solubility and physical properties that differ from the CP with the guanidine head group. Incorporation of hydrophobic groups, like piperidine, and hydrophilic group, like morpholine and aminoethoxyethanol, provide other CPS with varied properties.

In embodiments of the invention, the polymer need not be a conjugated polymer, which is generally ridged, but can be a non-conjugated polymer that has a flexible backbone. In embodiments of the invention, the polymer can have flexible side chains that enhance the water solubility of the polymer. In embodiments of the invention, the guanidine or protected guanidine is sufficient to impart water solubility. Synthetic and natural polymers that can be employed can be, but are not limited to, amine functionalized polymethacrylates and polyacrylates, branched and linear polyehtyleneimines, polyamidoamine, amine functionalized dendrimers, poly-L-lysine, chitosan, amine functionalized dextran, amine functionalized alginates, amine functionalized heparin, and amine functionalized oligo or polysaccharide.

Figure 17:
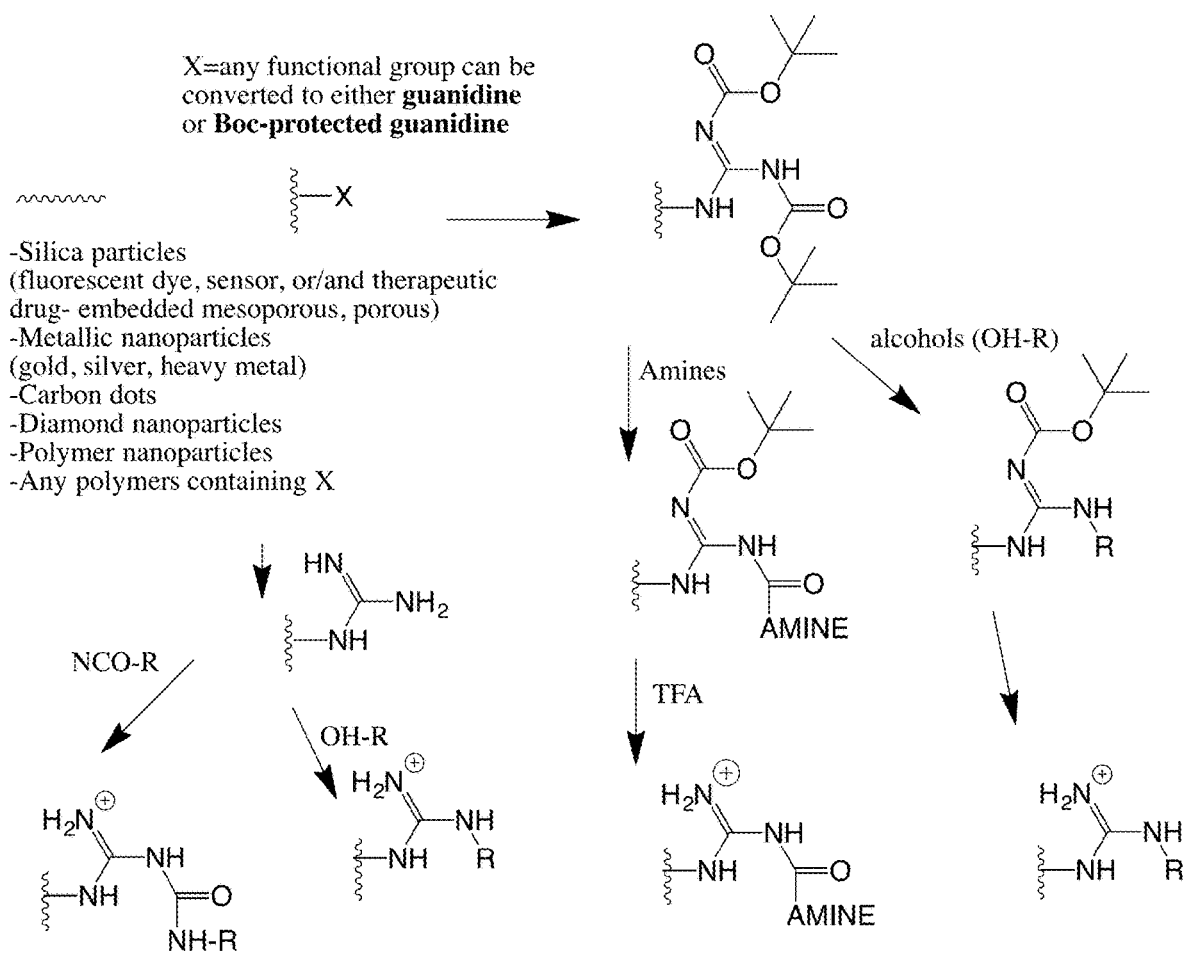
FIG. 17 shows a scheme for the various synthetic methods of formation of modulated guanidine functionalized nanoparticles or polymers, according to embodiments of the invention.

In embodiments of the invention, nanoparticles are used for efficient intracellular delivery and labeling after modulating surface properties to enhance their initial interaction following entry. As shown in FIG. 17, a nanoparticle bearing a surface functional group or a polymer with a functional group can be converted by reaction at the functional group to a guanidine, Boc-protected guanidine, or any other protected guanidine. The nanoparticles can be those that are metal oxides, metal carbides, metal nitrides, metals, diamond, or any other type of nanoparticle. The polymer can be in the form of a soluble polymer or can be a nanoparticle where the functional groups are of sufficient concentration at the nanoparticle surface to yield a nanoparticle that is decorated with the guanidine, Boc-protected guanidine, or any other protected guanidine. The nanoparticles can be of a single structure or a core-shell particle. The particles can inherently have surface functionality that react with guanidine or protected guanidine. The particle surface can be functionalized by reaction with an agent, for example, a silane coupling agent, such as, but not limited to, 3-aminopropyltrimethoxy silane, or thiol or disulfide containing alkyls with hydroxyl or amine groups for functionalization of metal nanoparticles.

In one embodiment, the polymeric system according to the subject invention comprises a modulated guanidine substituted polymer, the modulated guanidine substituted polymer comprising a guanidine moiety on a plurality of repeating units of a polymer. The modulation comprises a substituted amidinourea or amidinocarbamate or salt thereof.

In one embodiment, the polymeric system is a guanylurea functionalized molecular transporter, the guanylurea functionalized molecular transporter comprises a modulated guanidine substituted polymer, the modulated guanidine substituted polymer comprising a guanidine moiety on a plurality of repeating units of a polymer. The modulation comprises a substituted amidinourea or amidinocarbamate or salt thereof.

Advantageously, amidinoureas, also called guanylureas, are moieties with extended hydrogen bonding capacity as compared to guanidine. The interaction between the polymeric transporter system and cell membrane is enhanced by a polyvalent effect. The replacement of guanidine with guanylurea moieties in the polymeric system improves the binding of molecular transporters to the cell membrane and the delivery of cargo.

In one embodiment, the amidinocarbamate or salt thereof comprises a substituted or unsubstituted alky carbamate, aryl carbamate, alkylaryl carbamate or aryalkyl carbamante In one embodiment, the modulated guanidine substituted polymer comprises a conjugated polymer. In specific embodiments, the conjugated polymer comprises poly(phenyleneethynylene), poly(phenylenevinylene), poly(phenylene), poly(fluoreine), polythiophene, or any p-electron conjugated polymers.

In one embodiment, the guanylurea functionalized molecular transporter comprises a modulated guanidine substituted polymer, the modulated guanidine substituted polymer comprising a polymer chain that comprises one or more types of constituent units or repeating units.

Preferably, the repeating unit or monomer comprises or has the following structure:

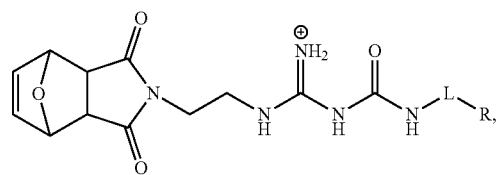

wherein L is a linker and can be null; and R is selected from, for example, hydrogen, alkyl, substituted alkyl, aryl, substituted aryl, heteroalkyl, substituted heteroalkyl, heteroaryl, substituted heteroaryl, cycloalkyl, substituted cycloalkyl, heterocycloalkyl, substituted heterocycloalkyl, cycloalkenyl, substituted cycloalkenyl, alkenyl substituted alkenyl, alkynyl, haloalkyl, acyl, amino, alkylamino, arylamino and hydroxylalkyl.

Preferably, R is selected from N-alkylamino; N-arylamino; N-(alkylaryl)amino; N-(aryalkyl)amino; N, N-dialkylamin; N, N-diarylamino; N, N-di(alkylaryl)amino; N, N-di(aryalkylamino); N-alkyl, N-arylamino; N-alkyl, N-(alkylaryl)amino; N-alkyl, N-(arylalkyl)amino; N-aryl, N-(alkylaryl)amino; N-aryl, N-(arylalkyl)amino; unsubstituted or substituted morpholine; unsubstituted or substituted pyrolidine; unsubstituted or substituted pyrrole; unsubstituted or substituted piperidine; unsubstituted or substituted ethyleneimine; unsubstituted or substituted indole; unsubstituted or substituted isoindole; unsubstituted or substituted carbazole; imidazole or substituted imidazole; purine or substituted purine; aminoethanol; amino terminal polyethylene oxide, substituted or unsubstituted alky carbamate, substituted or unsubstituted aryl carbamate, substituted or unsubstituted alkylaryl carbamate and substituted or unsubstituted aryalkyl carbamante. More preferably, R is selected from hexylamine (HA), benzylamine (BA), and aminoethoxyethanol (AEE).

In some embodiments, L is selected from alkyl, alkenyl, alkynyl, aromatics, heteroalkyl, heteroaryl, cycloalkyl, and heterocyclyl. Preferably, L is selected from C1-C10 alkyls, C2-C10 alkenyls, C2-C10 alkynyls, C3-C10 cycloalkyls, and C3-C10 heterocyclyls.

In one embodiment, the modulated guanidine substituted polymer comprises a homopolymer, the homopolymer comprising the following structure:

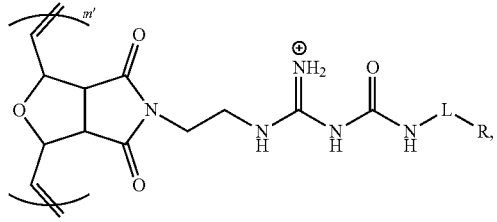

wherein L is a linker and can be null; m'≥2; and R is selected from hydrogen, alkyl, substituted alkyl, aryl, substituted aryl, heteroalkyl, substituted heteroalkyl, heteroaryl, substituted heteroaryl, cycloalkyl, substituted cycloalkyl, heterocycloalkyl, substituted heterocycloalkyl, cycloalkenyl, and substituted cycloalkenyl, alkenyl and substituted alkenyl, alkynyl, haloalkyl, acyl, amino, alkylamino, arylamino and hydroxylalkyl. Preferably, R is selected from N-alkylamino; N-arylamin; N-(alkylaryl)amino; N-(aryalkyl)amino; N, N-dialkylamino; N, N-diarylamino; N, N-di(alkylaryl)amino; N, N-di(aryalkylamino); N-alkyl, N-arylamino; N-alkyl, N-(alkylaryl)amino; N-alkyl, N-(arylalkyl)amino; N-aryl, N-(alkylaryl)amino; N-aryl, N-(arylalkyl)amino; unsubstituted or substituted morpholine; unsubstituted or substituted pyrolidine; unsubstituted or substituted pyrrole; unsubstituted or substituted piperidine; unsubstituted or substituted ethyleneimine; unsubstituted or substituted indole; unsubstituted or substituted isoindole; unsubstituted or substituted carbazole; imidazole or substituted imidazole; purine or substituted purine; aminoethanol; amino terminal polyethylene oxide, substituted or unsubstituted alky carbamate, substituted or unsubstituted aryl carbamate, substituted or unsubstituted alkylaryl carbamate and substituted or unsubstituted aryalkyl carbamante. More preferably, R is selected from HA, BA and AEE.

In one embodiment, the modulated guanidine substituted polymer comprises a homopolymer having a structure of

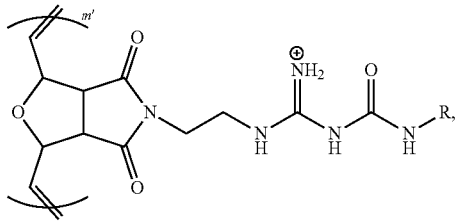

wherein m'≥2; and R is selected from HA, BA and AEE.

In specific embodiments, the modulated guanidine substituted polymer comprises a homopolymer selected from

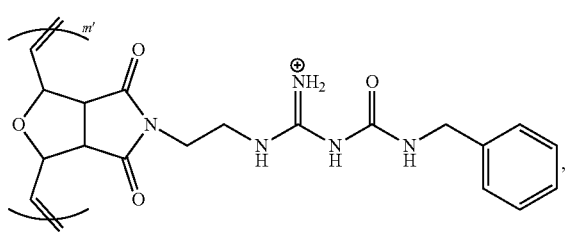

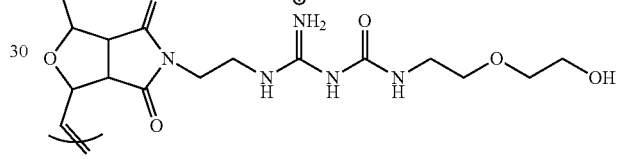

and

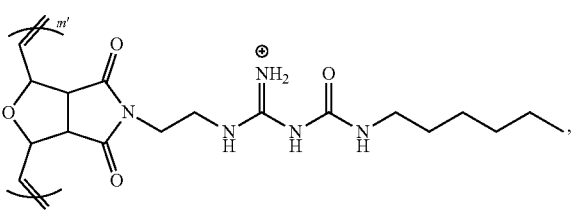

wherein m'≥2.

In one embodiment, the modulated guanidine substituted polymer is a copolymer comprises a polymer chain that comprises two or more types of constituent units or repeating units. In a further embodiment, the copolymer may be a bipolymer that is obtained by copolymerization of two monomer species, terpolymer that is obtained by copolymerization of three monomer species, or quaterpolymer that is obtained by copolymerization of four monomer species.

In one embodiment, the modulated guanidine substituted polymer of the subject invention further comprises one or more repeating units or monomer species selected from

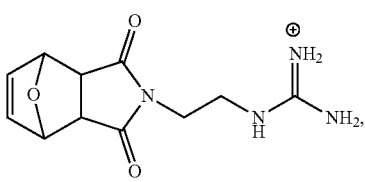

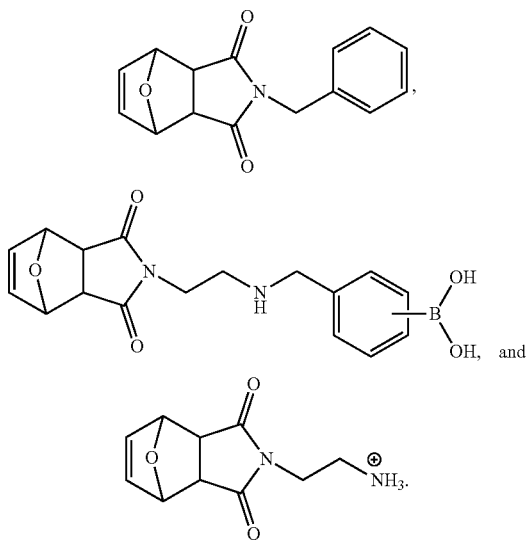

In one embodiment, the copolymer is an alternating copolymer, periodic copolymer, random copolymer or block copolymer. An alternating copolymer is a copolymer comprising two species of monomeric units distributed in alternating sequence, for example, -ABABABAB- or -(AB)n-. A random copolymer is a copolymer comprising two or more types of monomer species with each monomer residue located randomly in the polymer molecule, for example, -AAAABBBBABBA-, or -AAAABCBBCBACCBC-. A periodic copolymer a copolymer comprising two or more types of monomer species and has units arranged in a repeating sequence, for example, -(ABABBAAAABBB)n-, or -(AABCBAABBBCCAB)n-. A block copolymer is a copolymer comprising two or more blocks of different homopolymers chemically attached to each other, e.g., by covalent bonds. For example, a block copolymer having repeating units A and B may be arranged as -AAAAABBBBB- or -AAAAABBBBBAAAAA-.

In one embodiment, the modulated guanidine substituted polymer is a random copolymer comprising a polymer chain selected from

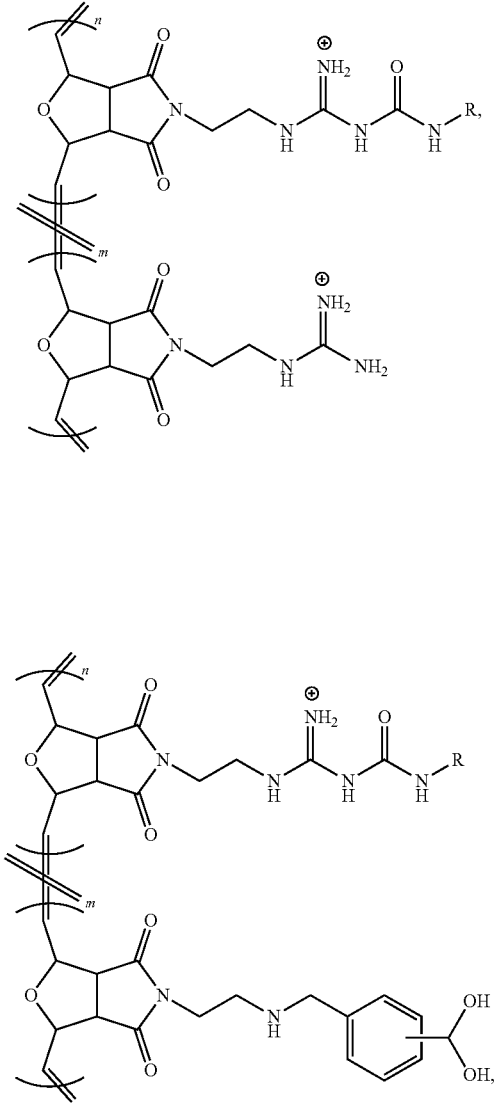

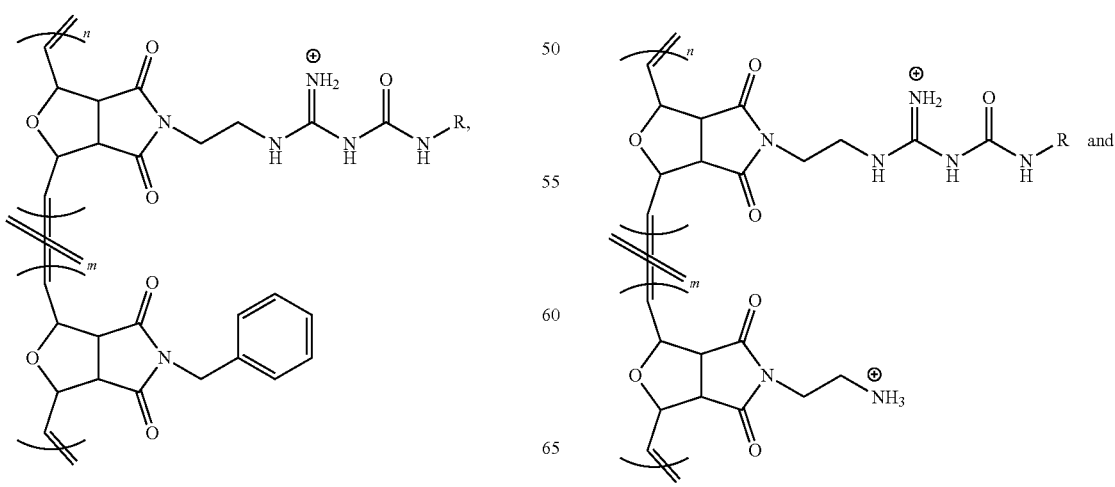

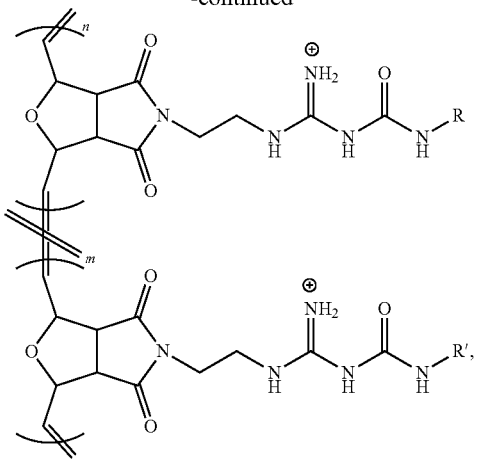

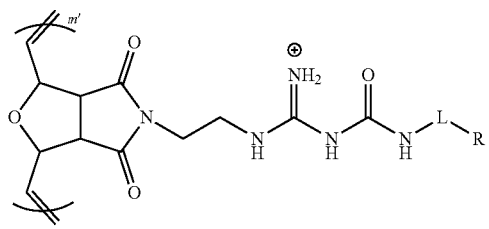

wherein m'≥2; L is a linker and can be null; and the polymer chain further comprises one or more blocks of homopolymer comprising monomer species selected from

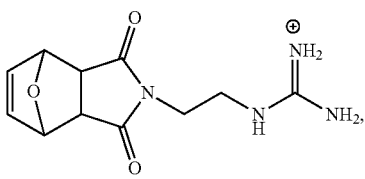 [SMILES: NC(=[NH2+])NCCN1C(=O)C2C3C=CC(O3)C2C1=O]

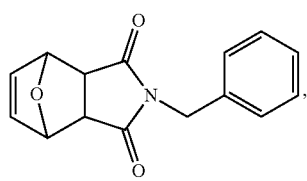 [SMILES: O=C1C2C3C=CC(O3)C2C(=O)N1Cc1ccccc1]

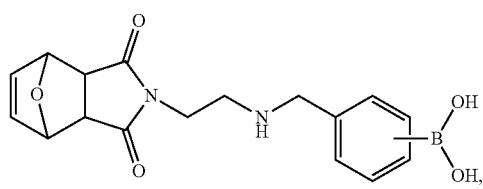

and

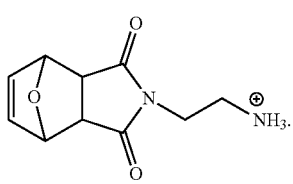

wherein ⇌ means that the two monomer species are randomly distributed; both m and n≥1; R and R' are independently selected from hydrogen, alkyl, substituted alkyl, aryl, substituted aryl, heteroaryl, substituted heteroaryl, heteroalkyl, substituted heteroalkyl, cycloalkyl, substituted cycloalkyl, heterocycloalkyl, substituted heterocycloalkyl, cycloalkenyl, and substituted cycloalkenyl, alkenyl and substituted alkenyl, alkynyl, haloalkyl, acyl, amino, alkylamino, arylamino and hydroxylalkyl; wherein m and n may be the same or different, and R and R' are different.

Preferably, R and R' are independently selected from N-alkylamino; N-arylamino; N-(alkylaryl)amino; N-(arylalkyl)amino; N, N-dialkylamino; N, N-diarylamino; N, N-di(alkylaryl)amino; N, N-di(aryalkylamino); N-alkyl,N-arylamino; N-alkyl, N-(alkylaryl)amino; N-alkyl, N-(arylalkyl)amino; N-aryl, N-(alkylaryl)amino; N-aryl, N-(arylalkyl)amino group; unsubstituted or substituted morpholine; unsubstituted or substituted pyrolidine; unsubstituted or substituted pyrrole; unsubstituted or substituted piperidine; unsubstituted or substituted ethyleneimine; unsubstituted or substituted indole; unsubstituted or substituted isoindole; and unsubstituted or substituted carbazole; and more preferably, R and R' are independently selected from HA, BA and AEE.

In one embodiment, the modulated guanidine substituted polymer is a block copolymer that induces nanostructure formation. By introducing a hydrophobic block, as in the block copolymers according to the subject invention, the hydrophobic segment may "collapse" in aqueous environment and create a micelle type nanostructure. The block copolymers of the subject invention were synthesized with various guanylurea modifications on one or more of the blocks.

Advantageously, by varying the local environment around the positive charge in the polymers using both hydrophobic and hydrophilic moieties, the polymers may be used to encapsulate drugs/small molecules. Additionally, these copolymers may be used to complex macromolecules such as proteins where the block structure may enhance the nanoparticle formation.

In one embodiment, the modulated guanidine substituted polymer is a block copolymer comprising a polymer chain that comprises one or more blocks of homopolymer, In one embodiment, the modulated guanidine substituted polymer is a block copolymer comprising a polymer chain that comprises one or more blocks of polymer comprising a plurality of monomers

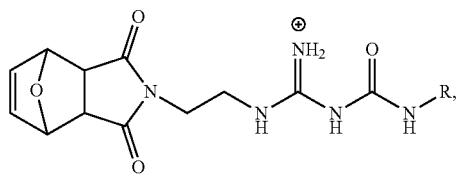

and the polymer chain further comprises one or more blocks of polymer comprising a plurality of monomer species selected from

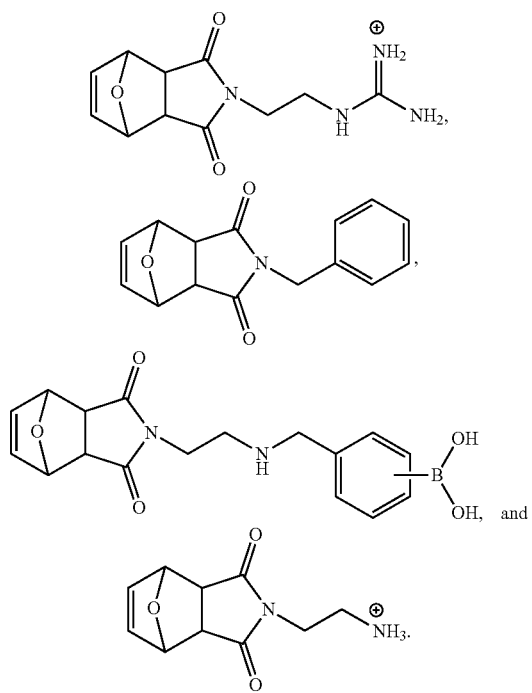

In one embodiment, the modulated guanidine substituted polymer is a block copolymer comprising a polymer chain of

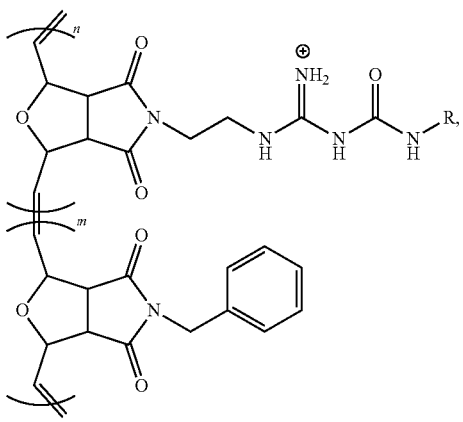

wherein m and n can be the same or different, and both m and n ≥ 1; and R is selected from hydrogen, alkyl, substituted alkyl, aryl, substituted aryl, heteroalkyl, substituted heteroalkyl, heteroaryl, substituted heteroaryl, cycloalkyl, substituted cycloalkyl, heterocycloalkyl, substituted heterocycloalkyl, cycloalkenyl, and substituted cycloalkenyl, alkenyl and substituted alkenyl, alkynyl, haloalkyl, acyl, amino, alkylamino, arylamino and hydroxylalkyl. Preferably, R is selected from N-alkylamino; N-arylamino; N-(alkylaryl) amino; N-(aryalkyl)amino; N, N-dialkylamino; N, N-diarylamino; N, N-di(alkylaryl)amino; N, N-di(aryalkylamino); N-alkyl, N-arylamino; N-alkyl, N-(alkylaryl)amino; N-alkyl, N-(arylalkyl)amino; N-aryl, N-(alkylaryl)amino; N-aryl, N-(arylalkyl)amino; unsubstituted or substituted morpholine; unsubstituted or substituted pyrolidine; unsubstituted or substituted pyrrole; unsubstituted or substituted piperidine; unsubstituted or substituted ethyleneimine; unsubstituted or substituted indole; unsubstituted or substituted isoindole; unsubstituted or substituted carbazole; imidazole or substituted imidazole; purine or substituted purine; aminoethanol; amino terminal polyethylene oxide, substituted or unsubstituted alky carbamate, substituted or unsubstituted aryl carbamate, substituted or unsubstituted alkylaryl carbamate and substituted or unsubstituted aryalkyl carbamante. More preferably, R is selected from HA, BA and AEE.

In a specific embodiment, the modulated guanidine substituted polymer is a block copolymer comprising a polymer chain selected from

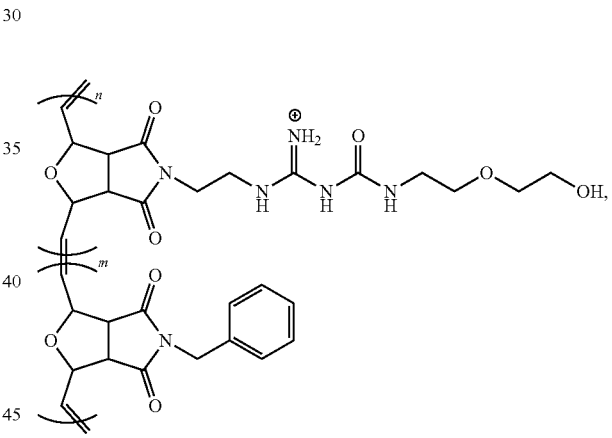

(Block-PN-co-AEE-BA)

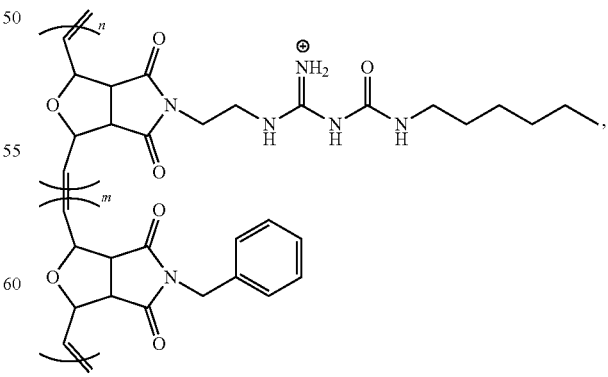

(Block-PN-co-HA-BA)

and

-continued

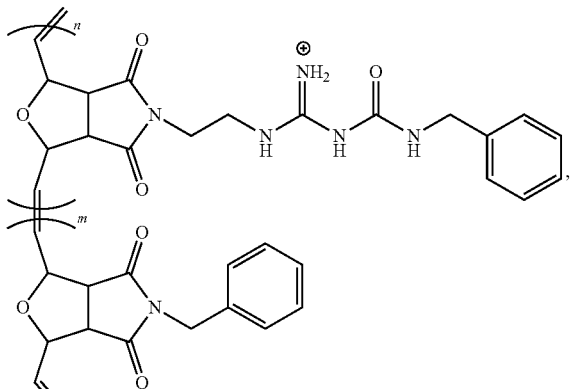

(Block-PN-co-BA-BA)

wherein m and n ≥ 1, and m and n can be the same or different.

In one embodiment, the homopolymer and/or copolymer of the subject invention comprises one or more boronic acid moieties. Boronic acids have strong binding affinity to biomolecules containing vicinal diols, such as sialic acid. Specifically, boronic acids can target low abundance biomolecules in glucose rich environments. Increased levels of sialic acid have been observed in many cancer cell lines. Thus, such copolymer containing boronic acid moieties may be used as a targeted therapy for cancer treatments.

In one embodiment, the modulated guanidine substituted polymer is a block copolymer comprising a polymer chain of wherein ⫝̸ means that the two monomer species may be randomly distributed; m, n and o can be the same or different, and m, n and o ≥ 1; and R is selected from hydrogen, alkyl, substituted alkyl, aryl, substituted aryl, heteroalkyl, substituted heteroalkyl, heteroaryl, substituted heteroaryl, cycloalkyl, substituted cycloalkyl, heterocycloalkyl, substituted heterocycloalkyl, cycloalkenyl, and substituted cycloalkenyl, alkenyl and substituted alkenyl, alkynyl, haloalkyl, acyl, amino, alkylamino, arylamino and hydroxylalkyl. Preferably, R is selected from N-alkylamino; N-arylamino; N-(alkylaryl)amino; N-(aryalkyl)amino; N, N-dialkylamino; N, N-diarylamino; N, N-di(alkylaryl)amino; N, N-di(aryalkylamino); N-alkyl, N-arylamino; N-alkyl, N-(alkylaryl)amino N-alkyl, N-(arylalkyl)amino; N-aryl, N-(alkylaryl)amino; N-aryl, N-(arylalkyl)amino; unsubstituted or substituted morpholine; unsubstituted or substituted pyrolidine; unsubstituted or substituted pyrrole; unsubstituted or substituted piperidine; unsubstituted or substituted ethyleneimine; unsubstituted or substituted indole; unsubstituted or substituted isoindole; unsubstituted or substituted carbazole; imidazole or substituted imidazole; purine or substituted purine; aminoethanol; amino terminal polyethylene oxide, substituted or unsubstituted alky carbamate, substituted or unsubstituted aryl carbamate, substituted or unsubstituted alkylaryl carbamate and substituted or unsubstituted aryalkyl carbamante. More preferably, R is selected from HA, BA and AEE.

In a specific embodiment, the modulated guanidine substituted polymer is a block copolymer comprising a polymer chain selected from

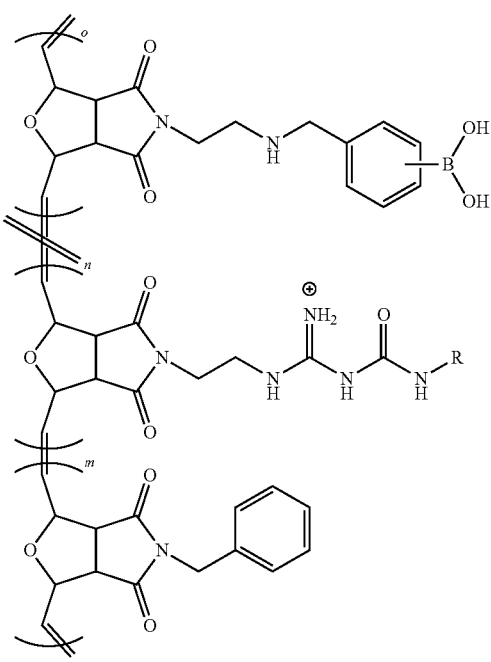

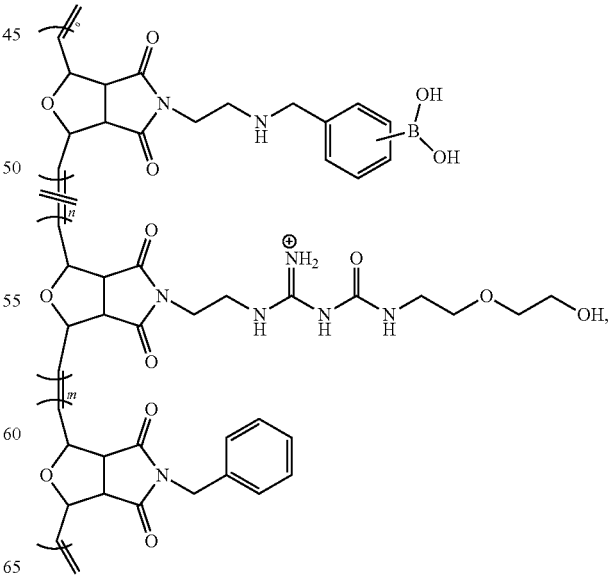

(Block-PN-co-AEE-BoronicAcid)

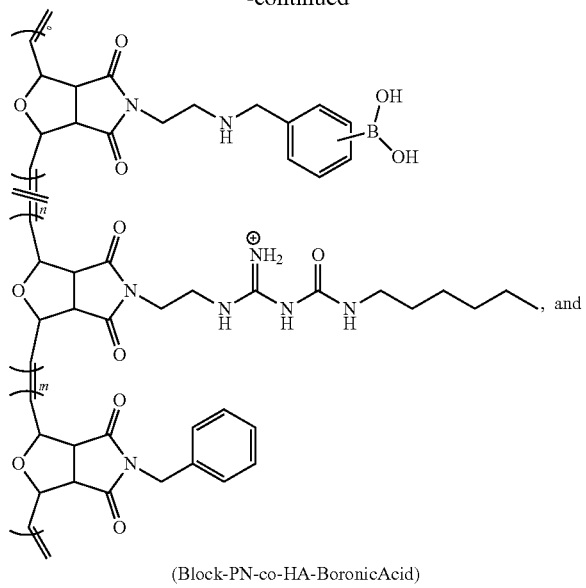

(Block-PN-co-HA-BoronicAcid)

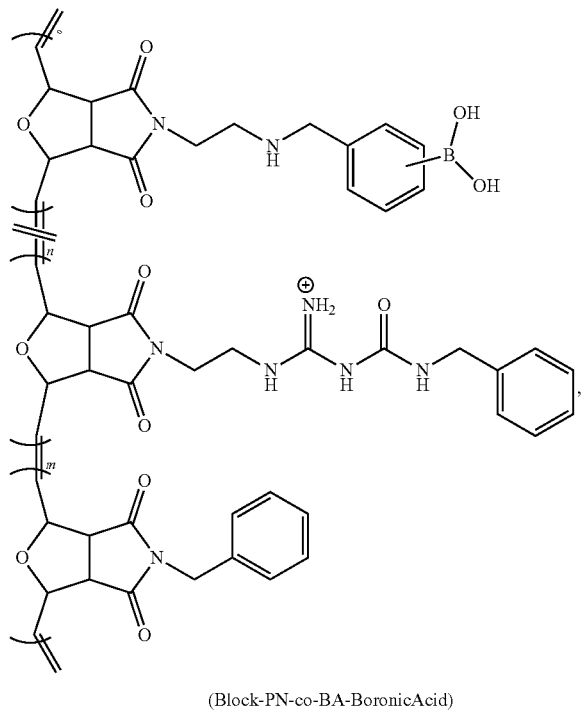

(Block-PN-co-BA-BoronicAcid)

wherein m, n and o≥1, and m, n and o can be the same or different; ⚌ means that the two monomer species may be randomly distributed.

Specifically, ligand affinity and specificity can be tuned by functionalizing boronic acid probes. Functionalization of phenylboronic acid derivatives changes the pKa of the boronic acid probes and the stability of tumor tissue in the acidic microenvironment.

In one embodiment, the modulated guanidine substituted polymer is a guanylurea boronic acid derivative that comprises a boronic acid moiety on the modulated guanidine moiety of the polymer according to the subject invention.

In a specific embodiment, the guanylurea boronic acid derivative comprises a polymer chain of

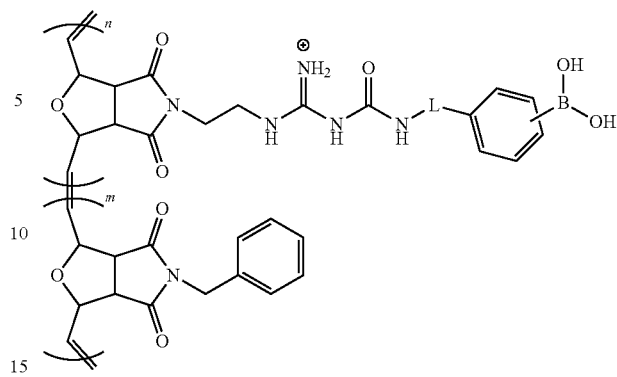

wherein m and n≥1, and m and n can be the same or different; and L is a linker and can be null. The linker may be alkyl or heteroalkyl, preferably, a short (e.g., C1-C10) alkyl or heteroalkyl.

In a specific embodiment, the guanylurea boronic acid derivative comprises a polymer chain of

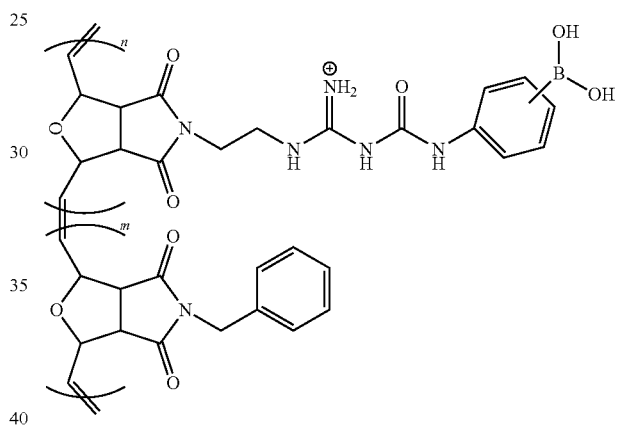

wherein m and n≥1, and m and n can be the same or different.

In one embodiment, the subject invention provides a nanomaterial that comprises a medulated guanidine substituted polymer of the subject invention conjugated to the surface of a nanoparticle. The nanoparticle comprises one or more selected from silica, alumina, titania, zinc oxide, tin oxide, silver oxide, cuprous oxide, cupric oxide, ceria, vanadium oxide zirconia, molybdenum, tungsten oxide, barium oxide, calcium oxide, iron oxide, and nickel oxide.

In one embodiment, the subject invention also provides a therapeutic formulation comprising the modulated guanidine substituted polymer or nanoparticle of the subject invention and a pharmaceutically acceptable carrier, wherein the therapeutic formulation further comprises one or more therapeutic agents, wherein one or more therapeutic agents are encapsulated by the modulated guanidine substituted polymer.

In one embodiment, the therapeutic formulation of the subject invention comprises a mixture/complex of the modulated guanidine substituted polymer or nanoparticle of the subject invention and one or more therapeutic agents, wherein the modulated guanidine substituted polymer or nanoparticle is mixed with the therapeutic agent at a concentration ratio ranging, for example, from about 1:1 to about 1000:1, from about 1:1 to about 900:1, from about 1:1 to about 800:1, from about 1:1 to about 700:1, from about 1:1 to about 600:1, from about 1:1 to about 500:1, from about 1:1 to about 400:1, from about 1:1 to about 300:1, from about 1:1 to about 200:1, from about 1:1 to about 100:1, from about 1:1 to about 90:1, from about 1:1 to about 80:1, from about 1:1 to about 70:1, from about 1:1 to about 60:1, from about 1:1 to about 50:1, from about 1:1 to about 40:1, from about 1:1 to about 30:1, from about 1:1 to about 20:1, or from about 1:1 to about 10:1.

"Pharmaceutically acceptable carrier" refers to a diluent, adjuvant or excipient with which the one or more active agents disclosed herein can be formulated. Typically, a "pharmaceutically acceptable carrier" is a substance that is non-toxic, biologically tolerable, and otherwise biologically suitable for administration to a subject, such as an inert substance, added to a pharmacological composition or otherwise used as a diluent, adjuvant or excipient to facilitate administration of the composition disclosed herein and that is compatible therewith.

Examples of carriers suitable for use in the pharmaceutical compositions are known in the art and such embodiments are within the purview of the invention. The pharmaceutically acceptable carriers and excipients, including, but not limited to, aqueous vehicles, water-miscible vehicles, non-aqueous vehicles, stabilizers, solubility enhancers, isotonic agents, buffering agents, suspending and dispersing agents, wetting or emulsifying agents, complexing agents, sequestering or chelating agents, cryoprotectants, lyoprotectants, thickening agents, pH adjusting agents, and inert gases. Other suitable excipients or carriers include, but are not limited to, dextran, glucose, maltose, sorbitol, xylitol, fructose, sucrose, and trehalose.

In one embodiment, the subject invention further provides methods for treating a cancer, the method comprising administering, to a subject in need of such treatment, an effective amount of the therapeutic formulation of the subject invention.

The term "subject" or "patient," as used herein, describes an organism, including mammals such as primates. Mammalian species that can benefit from the disclosed methods of treatment include, but are not limited to, apes, chimpanzees, orangutans, humans, and monkeys; domesticated animals such as dogs, cats; live stocks such as horses, cattle, pigs, sheep, goats, and chickens; and other animals such as mice, rats, guinea pigs, and hamsters.

The terms "treatment" or any grammatical variation thereof (e.g., treat, treating, etc.), as used herein, includes but is not limited to, the application or administration to a subject (or application or administration to a cell or tissue from a subject) with the purpose of delaying, slowing, stabilizing, curing, healing, alleviating, relieving, altering, remedying, less worsening, ameliorating, improving, or affecting the disease or condition, the symptom of the disease or condition, or the risk of (or susceptibility to) the disease or condition. The term "treating" refers to any indication of success in the treatment or amelioration of a pathology or condition, including any objective or subjective parameter such as abatement; remission; lessening of the rate of worsening; lessening severity of the disease; stabilization, diminishing of symptoms or making the pathology or condition more tolerable to the subject; or improving a subject's physical or mental well-being. Treating can also include preventing a condition or disorder, which, as used herein, means delaying the onset of, or progression of, a particular sign or symptom of the condition or disorder.

In one embodiment, the subject invention provides methods for targeted delivery of a compound or molecule, including therapeutic agents (e.g., drugs, antibodies, DNAs, RNAs such as siRNAs and miRNAs, peptides and proteins), into cells, preferably, cancer cells and epithelium cells, the method comprising contacting the cells with the polymeric system or therapeutic formulation of the subject invention.

In one embodiment, the subject invention provides methods for targeted delivery of a therapeutic agent into cells, preferably, cancer cells and epithelium cells, the method comprising contacting the cells with the modulated guanidine substituted polymer of the subject invention and the therapeutic agent.

In one embodiment, the subject invention provides methods for targeted delivery of a compound or molecule, including therapeutic agents (e.g., drugs, antibodies, DNAs, RNAs such as siRNAs and miRNAs, peptides and proteins), into the nuclei of cells, preferably, cancer cells and epithelium cells, the method comprising contacting the cells with the polymeric system or therapeutic formulation of the subject invention.

In one embodiment, the subject invention provides methods for targeted delivery of a therapeutic agent into the nuclei of cells, preferably, cancer cells and epithelium cells, the method comprising contacting the cells with the modulated guanidine substituted polymer of the subject invention and the therapeutic agent.

In one embodiment, the subject invention provides methods for transporting a compound or molecule, including therapeutic agents (e.g., drugs, antibodies, DNAs, RNAs such as siRNAs and miRNAs, peptides and proteins), across a biological membrane, the method comprising contacting the biological membrane with the polymeric system or formulation of the subject invention. The biological membrane may be, for example, cell membranes, organelle membranes, mucous membranes, basement membranes, and serous membranes.

In one embodiment, the subject invention provides methods for transporting a therapeutic agent across a biological membrane, the method comprising contacting the biological membrane with the modulated guanidine substituted polymer of the subject invention and the therapeutic agent.

In one embodiment, the subject invention further provides methods for altering/modulating gene expression in a cell, preferably, cancer cell and epithelium cell, the method comprising contacting the cell with the polymeric system or therapeutic formulation of the subject invention. Altering/modulating gene expression in a cell includes inhibiting or promoting gene expression in said cell.

In one embodiment, the subject invention further provides methods for altering/modulating gene expression in a cell, preferably, cancer cell and epithelium cell, the method comprising contacting the cell with the modulated guanidine substituted polymer of the subject invention and the therapeutic agent.

In one embodiment, the subject invention further provides methods for inhibiting gene expression in a cell, preferably, cancer cell and epithelium cell, the method comprising contacting the cell with the polymeric system or therapeutic formulation of the subject invention, wherein the polymeric system or therapeutic formulation comprises one siRNA targeting the gene of interest.

As used herein, the singular forms "a," "an," and "the" are intended to include the plural forms as well, unless the context clearly indicates otherwise. Further, to the extent that the terms "including," "includes," "having," "has," "with," or variants thereof are used in either the detailed description and/or the claims, such terms are intended to be inclusive in a manner similar to the term "comprising." The transitional terms/phrases (and any grammatical variations thereof), such as "comprising," "comprises," and "comprise," can be used interchangeably.

The transitional term "comprising," "comprises," or "comprise" is inclusive or open-ended and does not exclude additional, unrecited elements or method steps. By contrast, the transitional phrase "consisting of" excludes any element, step, or ingredient not specified in the claim. The phrases "consisting" or "consists essentially of" indicate that the claim encompasses embodiments containing the specified materials or steps and those that do not materially affect the basic and novel characteristic(s) of the claim. Use of the term "comprising" contemplates other embodiments that "consist" or "consisting essentially of" the recited component(s).

The term "about" or "approximately" means within an acceptable error range for the particular value as determined by one of ordinary skill in the art, which will depend in part on how the value is measured or determined, i.e., the limitations of the measurement system. For example, "about" can mean within 1 or more than 1 standard deviation, per the practice in the art. Alternatively, "about" can mean a range of up to 0-20%, 0 to 10%, 0 to 5%, or up to 1% of a given value. Alternatively, particularly with respect to biological systems or processes, the term can mean within an order of magnitude, preferably within 5-fold, and more preferably within 2-fold, of a value. Where particular values are described in the application and claims, unless otherwise stated the term "about" meaning within an acceptable error range for the particular value should be assumed. In the context of compositions containing amounts of concentrations of ingredients where the term "about" is used, these values include a variation (error range) of 0-10% around the value (X±10%).

As used herein, each m', m, n, and o is intended to include ≥2, ≥3, ≥4, ≥5, ≥6, ≥7, ≥8, ≥9, ≥10, ≥11, ≥12, ≥13, ≥14, ≥15, ≥16, ≥17, ≥18, ≥19, ≥20, ≥21, ≥22, ≥23, ≥24, ≥25, ≥26, ≥27, ≥28, ≥29, ≥30, ≥31, ≥32, ≥33, ≥34, ≥35, ≥36, ≥37, ≥38, ≥39, ≥40, ≥41, ≥42, ≥43, ≥44, ≥45, ≥46, ≥47, ≥48, ≥49, ≥50, ≥51, ≥52, ≥53, ≥54, ≥55, ≥56, ≥57, ≥58, ≥59, ≥60, ≥61, ≥62, ≥63, ≥64, ≥65, ≥66, ≥67, ≥68, ≥69, ≥70, ≥71, ≥72, ≥73, ≥74, ≥75, ≥76, ≥77, ≥78, ≥79, ≥80, ≥81, ≥82, ≥83, ≥84, ≥85, ≥86, ≥87, ≥88, ≥89, ≥90, ≥91, ≥92, ≥93, ≥94, ≥95, ≥96, ≥97, ≥98, ≥99, and ≥100.

The recitation of a listing of chemical groups in any definition of a variable herein includes definitions of that variable as any single group or combination of listed groups. The recitation of an embodiment for a variable or aspect herein includes that embodiment as any single embodiment or in combination with any other embodiments or portions thereof.

EXAMPLES

Methods and Materials

Materials

Reagents and solvents were purchased from Fisher Scientific and used without further purification. Deuterated solvents were purchased from Cambridge Isotope Laboratories (Cambridge, Mass.). All solutions were prepared using deionized (DI) water (~18MΩ) from water purification system (Ultra Purelab system, ELGA/Siemens). The number average molecular weight ($M_n$), weight average molecular weight ($M_w$), and polydispersity index (PDI=Mw/Mn) of CPs were determined by gel permeation chromatography (GPC) against polystyrene standards using a Shimadzu high performance liquid chromatography (HPLC) system fitted with PLgel 5 μm MIXED-D columns and SPD-20A ultraviolet-visible (UV-vis) detector at a flow rate of 1.0 mL/min. Samples for GPC, small amount (~100 μL) of polymer in dimethylformamide (DMF) or dichloromethane (DCM) was diluted with 1 mL of HPLC grade THF and then filtered through a 0.45 μM polytetrafluoroethylene (PTFE) syringe filter prior injection. UV-vis spectra were recorded using a Varian Cary 50 Bio spectrophotometer. Fluorescence spectra were obtained using a FluoroLog-3 Spectrofluorometer (Jobin Yvon/Horiba). 9,10-diphenylanthracene (QY=0.9) in cyclohexane was used as a fluorescence standard. Fourier transform infrared (FTIR) spectra were recorded on a PerkinElmer Spectrum 100 FTIR Spectrometer. Fine polymer powders were directly mounted on an attenuated total reflection (ATR) cell of the spectrometer. Nuclear magnetic resonance (NMR) spectra were recorded on a 400 MHz Avance Bruker NMR spectrometer. Chemical shifts were reported in parts per million (ppm) for 1H NMR on the δ scale based on the middle peak (δ=2.50 ppm) of the dimethylsulfoxide (DMSO-d6) solvent as an internal standard.

Monomer Synthesis

Synthesis of monomer A. Guanidinium-containing aryldiiodide monomer A was synthesized as described in Ahmed et al., *Bioconjugate Chem.* 2018, 29 (4), 1006-9.

Synthesis of monomer B. A round-bottomed flask was charged with compound A (2.00 g, 1.96 mmol), trimethylsilylacetylene (0.77 g, 7.84 mmol), $PdCl_2(PPh_3)_2$ (137.6 mg, 0.20 mmol), and CuI (18.6 mg, 0.10 mmol). The round-bottomed flask was evacuated and filled with $N_2$ three times. A solution of tetrahydrofuran (THF) and diisopropylamine (DIPA) was mixed in a 4:1 ratio (v/v) and degassed with $N_2$ for 10 minutes, and then 50 mL was transferred to the ROUND-BOTTOMED FLASK via a cannula. The reaction mixture was stirred at room temp for 3 h equipped with a $N_2$ balloon. The yellow reaction mixture was filtered to remove insoluble particles and THF was distilled from the mixture in vacuo. The reaction mixture was dissolved in DCM and washed with 1M $NH_4Cl$ two times followed by brine. Column chromatography using 30% ethyl acetate in hexane yielded a trimethylsilyl (TMS)-protected compound as a white solid (1.22 g, 65% yield). $^1H$ NMR (400 MHz), $CDCl_3$, δ: 11.46 (s, 0.95H), 8.67 (s, 0.96H), 7.21 (s, 0.98H), 4.1 (t, J=4.4 Hz, 2H), 3.88 (t, J=4.8 Hz, 2H), 3.78 (t, J=4.8 Hz, 2H), 3.66 (q, J=5.2 Hz, 2H), 1.50 (s, 9.1H), 1.45 (s, 9.21H), 0.10 (s, 18.2H).

In a round-bottomed flask, the trimethylsilyl (TMS)-protected compound (1.00 g, 1.04 mmol), and potassium carbonate (0.36 g, 2.60 mmol) were mixed in methanol (40 mL). The round-bottomed flask was then stirred at r.t. for 20 min. Upon confirmation of TMS deprotection by TLC, the solvent was dried in vacuo. The reaction mixture was then purified by short-path column chromatography using 35% ethyl acetate in hexane, yielding a yellowish solid (0.51 g, 60% yield). $^1H$ NMR (400 MHz), $CDCl_3$, δ: 11.45 (s, 1H), 8.67 (s, 1H), 6.98 (s, 1H), 4.15 (t, J=4.4 Hz, 2H), 3.86 (t, J=4.8 Hz, 2H), 3.75 (t, J=4.8 Hz, 2H), 3.65 (q, J=5.2 Hz, 2H), 3.35 (s, 1H), 1.50 (s, 9H), 1.45 (s, 9H). $^{13}C$ NMR (400 MHz), $CDCl_3$, δ: 156.4, 154.2, 153.1, 118.3, 113.8, 83.2, 83.1, 79.6, 79.4, 70.0, 69.8, 69.4, 40.9, 28.4, 28.2. FT-IR (neat): 3330.9, 3281.4, 2975.3, 2930.5, 1720.2, 1636.1, 1613.1, 1568.2, 1495.8, 1410.3, 1319.7, 1222.7, 1129.0, 1049.9 $cm^{-1}$. HRMS $[M+H]^+$=817.4342 (theoretical) and 817.4365 (observed).

Synthesis of monomer 5. The Diels-Alder adduct 1 was synthesized according to previously published procedures. In short, furan and maleic anhydride were stirred in toluene at 80° C. The product precipitated at room temperature and was used without further purification with a yield of 80%.

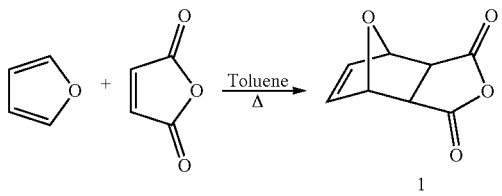

Ethylenediamine was single side N-Boc protected by addition of 0.1 eq of di-tert-buyl decarbonate dropwise over 24 h. Product was purified by extraction with water (3×) and brine (1×). Compound was obtained as a yellow oil at 83% yield.

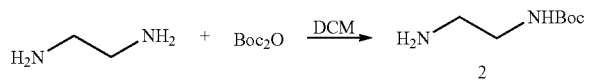

Compounds 3-4 were synthesized using modified literature procedures. 1 was dissolved in methanol and 1.5 eq of each amine and 1 eq of triethylamine were added. The reaction was complete after 24 h. Compound 3 precipitated at room temperature and 4 was purified by extraction and collected in DCM. Yields for 3 and 4 were 50% and 68% respectively.

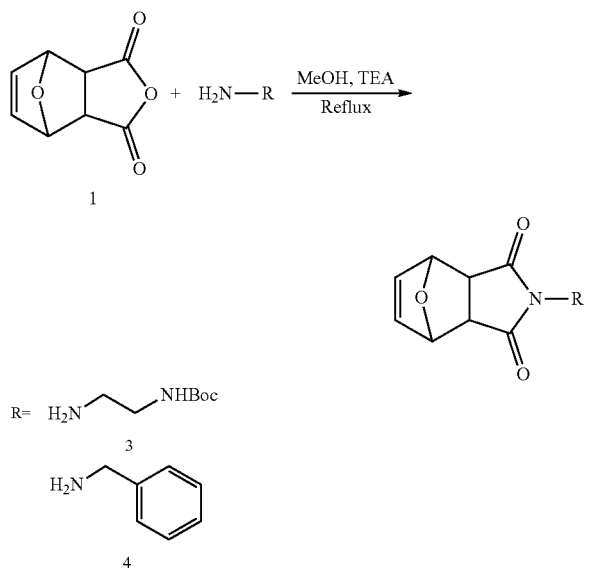

Compound 3 was deprotected in 1:1 mixture of dichloromethane and TFA and precipitated into diethyl ether. The precipitate was dried, dissolved in a 9:1 mixture of acetonitrile and water along with 3 eq of TEA, 1.5 eq of N,N'-Di-Boc-1H-pyrazole-1-carboxamidine and allowed to react overnight at room temperature. The reaction mixture was diluted with DCM and extracted with water (3×). Monomer 5 was purified by recrystallization using dichloromethane and methanol system affording pure compound at 68% yield.

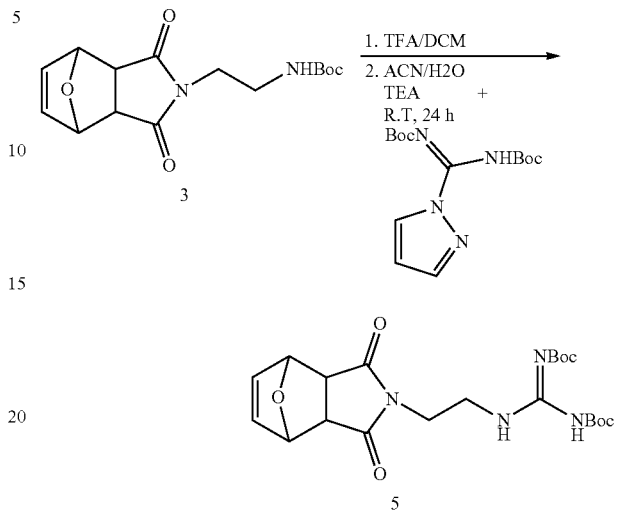

Homo Polymer Synthesis

PN-G-R

Boc-protected guanidine polymers were synthesized by dissolving monomer 5 in dry DCM and adding varying molar equivalents of Grubbs' $3^{rd}$ gen catalyst. The solutions were stirred for 45 minutes before the addition of 1 mL of ethyl vinyl ether to terminate the polymerization. The polymer solutions were precipitated (3×) into diethyl ether and precipitates were collected and dried.

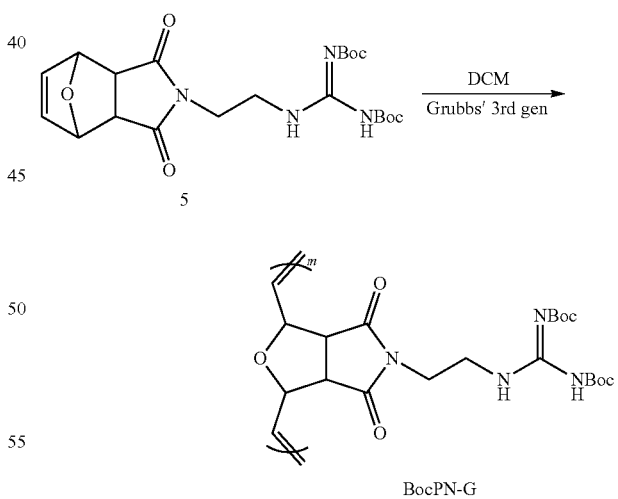

Boc-protected homopolymer was either deprotected (PN-G) or modified to PN-G-R (R=BA, HA, AEE or other primary/secondary amines) by reaction in THF at 75° C. 1.5 eq of the corresponding amine was added to the polymer solution and left stirring for 24 hours. The resulting polymer was purified by precipitation (3×) into diethyl ether. The resulting precipitates were deprotected in a 1:1 DCM:TFA mixture.

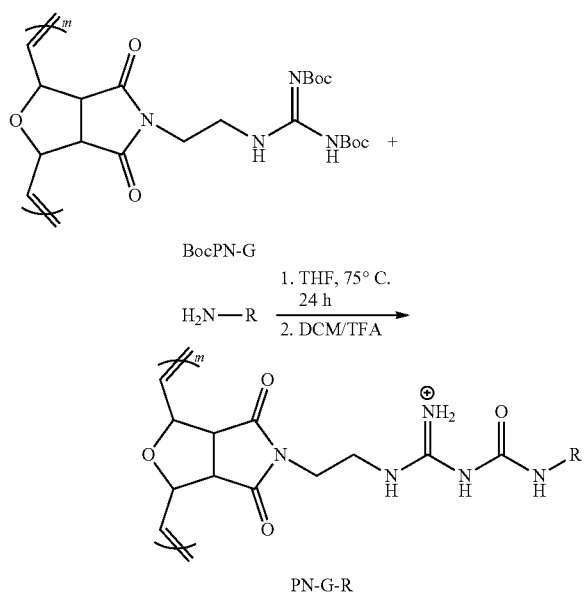

Guanidine Homo Polymer (Boc-Protected Poly-1)

Figure 18:
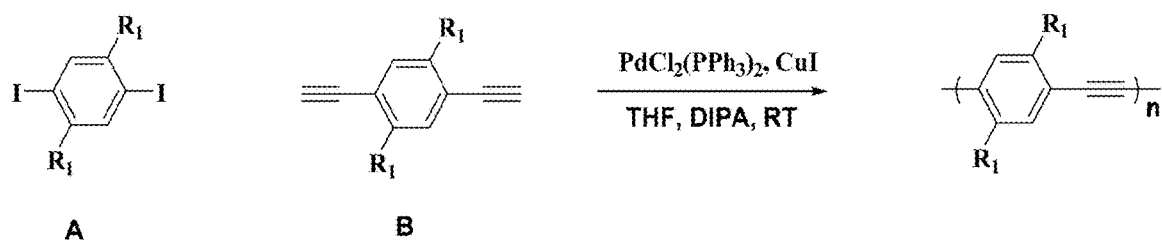
FIG. 18 shows a reaction scheme for the preparation of a G-CP.
Figure 18:
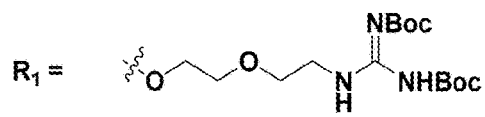

As indicated in the reaction scheme of FIG. 18, a Schlenk flask was charged with guanidine substituted p-diiodiaromatic monomer A 50 mg, 0.04 mmol, guanidine substituted p-diacetylenodiaromatic comonomer B (40.0 mg, 0.04 mmol), $PdCl_2(PPh_3)_2$ (3.43 mg, 0.005 mmol), and CuI (0.47 mg, 0.0024 mmol). The Schlenk flask was evacuated and filled with $N_2$. A solution of tetrahydrofuran (THF) and diisopropylamine (DIPA) was mixed in 4:1 volume ratio and degassed with $N_2$, and 2 mL was transferred to the Schlenk flask via a cannula. The reaction mixture was stirred at RT for 16 h. The solution was filtered through a glass wool filter and added dropwise to methanol to precipitate the GCP. The supernatant was decanted; the precipitate was re-dissolved in dichloromethane (0.5 mL) and purification method was repeated using methanol. The resulting Boc protected polymer in DCM was characterized by gel permeation chromatography (GPC) and their absorption/emission profile was measured. The final polymer was allowed to dry under high vacuum for 16 h before $^1H$ NMR characterization. $^1H$ NMR (400 MHz), $CDCl_3$, δ: 11.46 (s, 1H), 8.62 (s, 1H), 7.05 (s, 1H), 4.24 (s, 2H), 3.91 (s, 2H), 3.74 (s, 2H), 3.62 (s, 2H), 1.48 (s, 9H), 1.45 (s, 9H). FT-IR (neat): 3329.4, 3131.7, 2975.3, 2931.3, 1720.1, 1635.2, 1614.0, 1567.7, 1503.9, 1411.8, 1364.5, 1319.8, 1280.5, 1249.7, 1131.0, 1048.8 $cm^{-1}$. GPC: Mn=13,500 g/mol, Mw=18,000 g/mol, PDI=1.30, UV-Vis (THF) $\lambda_{max}$=442 nm, Fluo $\lambda_{max}$=469 nm.

Guanidine-DIPA (PG-D)

Figure 19:
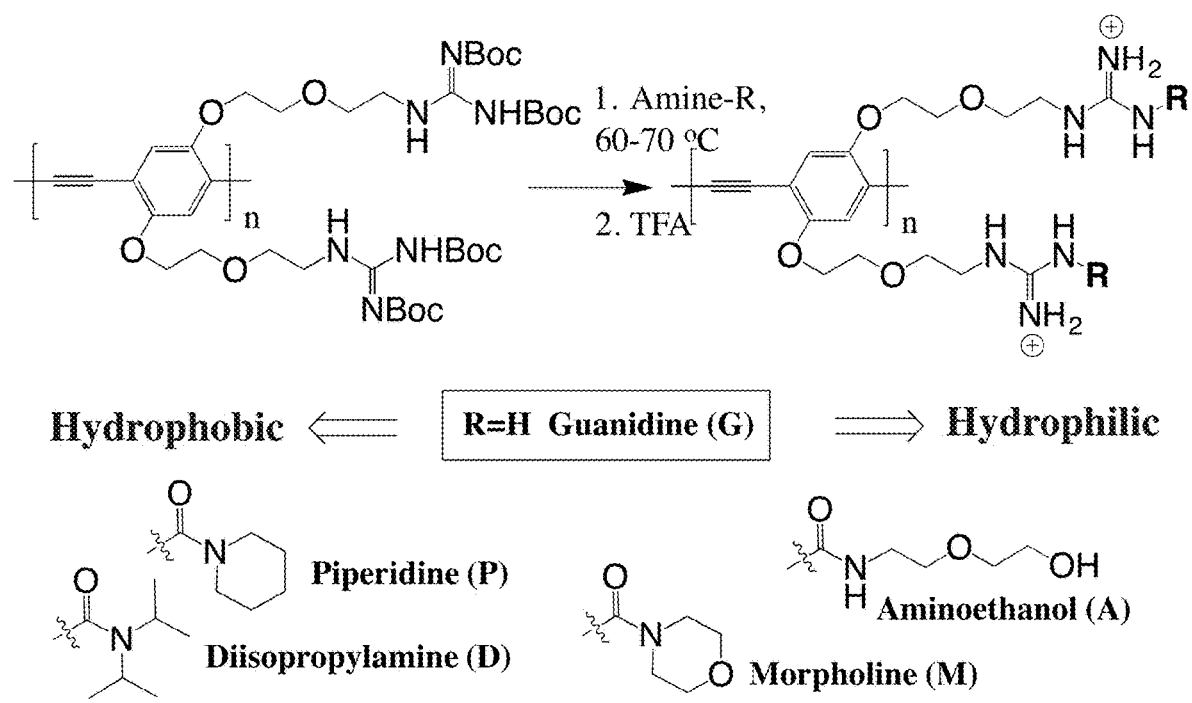
FIG. 19 shows a reaction scheme for the preparation of a modulated G-CP, according to an embodiment of the invention.

As illustrated in FIG. 19, using the general polymerization procedure for Boc-protected Poly-1, above, through the addition of the 4:1 THF/DIPA mixture a latent reaction mixture was formed with the Boc-protected Poly-1. The reaction mixture was heated at 80° C. for 16 h. Upon precipitation, as above, an overall yield of 63% (26.9 mg) was achieved. The resulting polymer in DCM was characterized by gel permeation chromatography (GPC) and its absorption/emission profiles were measured. The final polymer was allowed to dry under high vacuum for 16 h before $^1H$ NMR characterization.

$^1H$ NMR (400 MHz), $CDCl_3$, δ: 12.42 (s, 0.92H), 8.21 (s, 0.88H), 7.05 (s, 0.88H), 4.23 (s, 2H), 3.90 (s, 2H), 3.75 (s, 3.46H), 3.60 (s, 0.61H), 3.54 (s, 1.92H), 1.42 (s, 9.23H), 1.23 (s, 12.25H) GPC: Mn=13155 g/mol, Mw=22363 g/mol, PDI=1.70, UV-Vis (THF) $\lambda_{max}$=434 nm, Fluo $\lambda_{max}$=472 nm.

Boc-Deprotection to Poly-1

A solution of Boc-protected Poly-1 in DCM (1.00 mL) was treated with trifluoroacetic acid (TFA) at room temperature for 48 hours. The solvent was removed under reduced pressure and the crude material was dissolved in minimum amount of dimethylformamide (DMF) to have a clear homogeneous solution. The polymer solution in DMF was transferred to diethyl ether, resulting in yellowish fiber like precipitates that were collected by decantation. The polymer was dissolved in DMF and then re-precipitated in ethyl acetate (EA). This process was repeated twice and the final Boc-deprotected polymer was collected by decantation followed by vacuum dry. After drying in a high vacuum, the final deprotected polymer was a yellow gel (74.6% yield) with complete Boc-deprotection confirmed by $^1H$ NMR. $^1H$ NMR (400 MHz, DMSO-$d_6$, δ): 8.13 (s, 1H), 7.92 (s, 2H), 7.27 (s, 2H), 6.87 (s, 1H), 5.77 (s, 1H), 5.03 (s, 1H), 4.30 (s, 2H), 3.98 (s, 2H), 3.59 (s, 4H), 3.50 (m, 6H), 2.98 (m, 10H), 2.87 (s, 1H), 2.01 (m, 6H). FT-IR (neat): 3360.36, 2160.37, 1736.79, 1681.18 $cm^{-1}$. UV-Vis (DMSO) $\lambda_{max}$=434 nm, Fluo $\lambda_{max}$=490 nm, QY=0.08.

Guanidine-Morpholine (PG-M)

A Schlenk flask was charged with GCP (10 mg, 0.012 mmol) and Morpholine (2.57 mg, 0.03 mmol). The Schlenk flask was evacuated and filled with $N_2$. A degassed tetrahydrofuran (THF) (1.5 mL) was transferred to the Schlenk flask via a cannula. The reaction was stirred at 80° C. for 16 h. The viscous polymer solution was filtered through glass wool followed by precipitation in diethyl ether and re-precipitating in methanol. The final polymer was yellow gel (7.72 mg with 76% yield). $^1H$ NMR (400 MHz), $CDCl_3$, δ: 12.2 (s, 1H), 8.3 (s, 1.05H), 7.04 (s, 0.94H), 4.22 (s, 2H), 3.90 (s, 2.30), 3.74 (s, 4.47H), 3.60 (s, 4.06H), 3.52 (s, 4.21H), 1.42 (s, 9.90H). GPC: Mn=12364 g/mol, Mw=18598 g/mol, PDI=1.50. UV-Vis (THF) $\lambda_{max}$=428 nm, Fluo $\lambda_{max}$=469 nm.

Guanidine-Piperidine (PG-P)

A Schlenk flask was charged with GCP (10 mg, 0.012 mmol) and Piperidine (2.51 mg, 0.03 mmol). The Schlenk flask was evacuated and filled with $N_2$. Degassed tetrahydrofuran (THF) (1.5 mL) was transferred to the Schlenk flask via a cannula. The reaction was stirred at 80° C. for 16 h. The viscous polymer solution was filtered through glass wool followed by precipitation in diethyl ether and re-precipitating in methanol. The final polymer was yellow gel (5.36 mg with 53% yield). $^1H$ NMR (400 MHz), $CDCl_3$, δ: 12.30 (s, 0.98H), 8.22 (s, 0.91H), 7.05 (s, 0.86H), 4.22 (s, 1.92H), 3.90 (s, 1.99H), 3.74 (s, 2.15H), 3.65 (s, 2.42H), 3.59 (s, 0.83H), 3.53 (s, 1.78H), 3.47 (s, 2.71H) 1.42 (s, 9H). GPC: Mn=14606 g/mol, Mw=27751 g/mol, PDI=1.90. UV-Vis (THF) $\lambda_{max}$=436 nm, Fluo $\lambda_{max}$=461 nm.

Guanidine-Aminoethoxyethanol (Poly-1)

A Schlenk flask was charged with Guanidine Homo Polymer (10 mg, 0.012 mmol) and Aminoethoxyethanol (3.1 mg, 0.03 mmol). The Schlenk flask was evacuated and filled with $N_2$. A degassed tetrahydrofuran (THF) (1.5 mL) was transferred to the Schlenk flask via a cannula. The reaction was stirred at 80° C. for 16 h. The viscous polymer solution was filtered through glass wool followed by re-precipitation in diethyl ether and re-precipitating in methanol. The final polymer was yellow gel (8.5 mg with 82.5% yield). $^1H$ NMR (400 MHz), $CDCl_3$, δ: 12.05 (s, 0.73H), 8.27 (s, 0.63H), 7.04 (s, 0.87H), 6.03 (s, 0.55H), 4.22 (s, 2H), 3.90 (s, 2.38H), 3.72 (s, 5.42H), 3.53 (s, 8.26H), 3.36 (s, 02.31H), 1.42 (s, 7.22H); $^1H$ NMR (400 MHz, DMSO-$d_6$, δ): 10.03

(s, 1H), 9.25 (s, 1H), 8.60 (s, 2H), 7.53 (s, 2H), 4.38 (s, 1H), 4.03 (s, 1H), 3.81 (s, 2H). GPC: Mn=13767 g/mol, Mw=19529 g/mol, PDI=1.41. UV-Vis (THF) $\lambda_{max}$=435 nm, Fluo $\lambda_{max}$=465 nm; UV-Vis (DMSO) $\lambda_{max}$=434 nm, Fluo $\lambda_{max}$=494 nm, QY=0.20.

Random Copolymer Synthesis

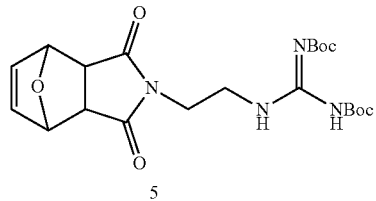
5

+

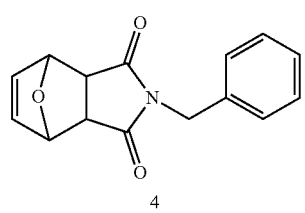
4

1. DCM/G3 Cat.
2. DCM/TFA
→

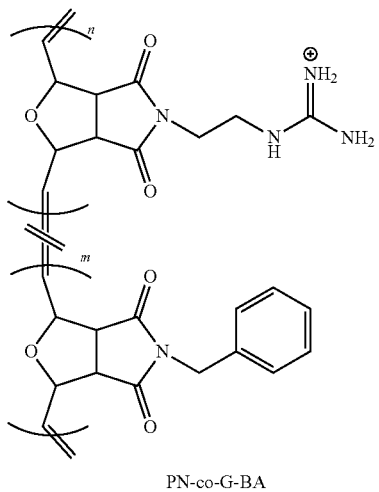
PN-co-G-BA

Random copolymer PN-co-G-BA was synthesized by mixing both respective monomers in DCM and adding varying molar equivalents of Grubbs 3$^{rd}$ gen catalyst. Polymerizations were terminated by the addition of 1 mL of ethyl vinyl ether and precipitation into diethyl ether (3×), followed by deprotection in TFA.

Block Copolymer Synthesis

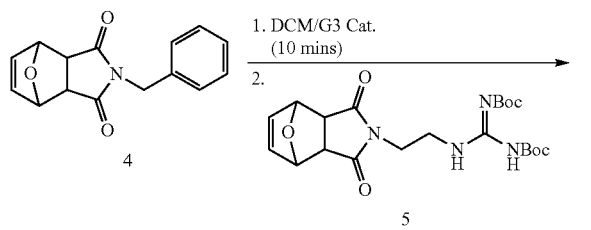

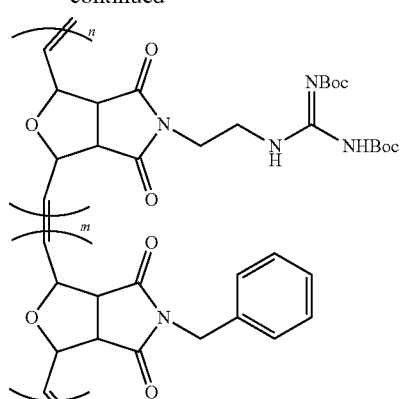
Boc-Block-PN-co-G-BA

Block copolymer Boc-Block-PN-co-G-BA was synthesized by stirring 4 with varying molar ratios of Grubbs catalyst for 10 minutes prior to the addition of monomer 5. Polymerization was terminated with ethyl vinyl ether and precipitated (3×) in diethyl ether.

[Boc-Block-PN-co-G-BA structure]

+

H$_2$N—R   1. THF, 75° C. 24 h
           2. DCM/TFA
→

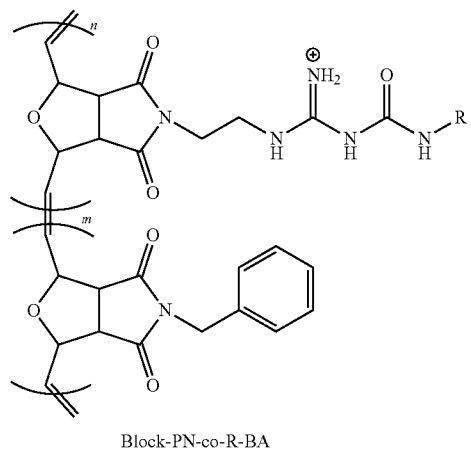
Block-PN-co-R-BA

Boc-Block-PN-co-G-BA was either deprotected to yield Block-PN-co-G-BA or reacted with varying amines in THF followed by deprotection to yield Block-PN-co-R-BA where R=AEE, HA, or BA.

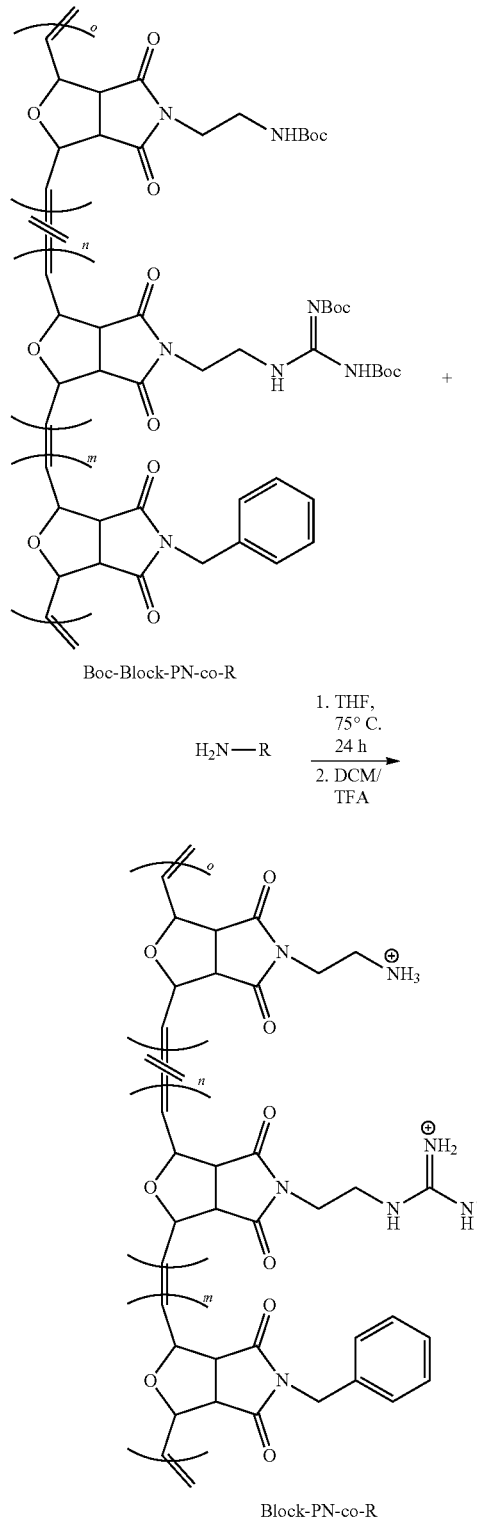

Boc-Block-PN-co-R

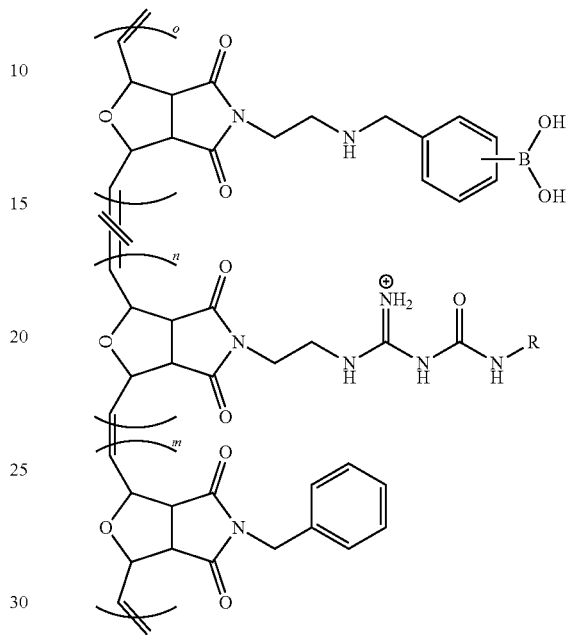

Boc-Block-PN-co-R above was synthesized in similar manner as previous polymers using varying molar ratios of Grubbs catalyst. This polymer was deprotected or modified using guanylurea modification to yield Block-PN-co-R where R=G, AEE, HA or BA. These polymers were modified with various phenyl boronic acid derivatives to yield the final Block-PN-co-R-Boronic Acid where the boronic acid position varies on the phenyl group.

Physical and Photophysical Properties of CPs

For the data tabulated in Table 1, below, the UV absorbance and emission spectra of Poly-1 and Poly-2 were determined in DMSO and 95% water+5% DMSO. In a good solvent, such as DMSO, polymer absorbance and emission did not change. But in a poor solvent, such as water, their emission spectra were significantly changed. FIGS. 6A and 6B show the UV absorbance and emission spectra. The HD and zeta potential of Poly-1 and Poly-2 were determined using Nanoparticle Tracking Analysis (NTA) and Dynamic Light Scattering (DLS), respectively. For NTA and DLS, all cuvette, pipette, and pipette tips were autoclaved. The working area was cleaned with 70% ethanol to avoid cross contamination. Stock polymer samples were prepared at a concentration of 100 µM in DMSO solvent. 10 µL of a stock polymer solution in DMSO was added to 90 µL of RNAse water. The polymer solution in DMSO-water added to 11.11 nM and 900 µL siRNA containing RNAse water. The mixture of polymer and siRNA solution was gently pipetted, and 1 mL sample solution was then injected to the NTA chamber, and images of scattering particles in the sample were collected for 90 seconds. Software identified each individual particle and tracked its motion throughout the duration of the recorded video. The measured particle displacement is a function of Brownian motion, which is related to the particle size through the Stokes-Einstein equation. The final data was collected under the detection threshold at 4, to obtain the acceptable data meeting the concentration requirements. All measurements were performed in triplicate at 25° C. using a temperature controller. The values in Table 2, below, are averaged from three independent measurements. Selected representative NTA graphs are presented in FIGS. 7A and 7B.

TABLE 1

Physical and Photophysical Properties of CPs

| Poly | $Mn^a$ | $PDI^b$ | $n^c$ | $A_{max, abs}$ $(nm)^d$ | $A_{max, em}$ $(nm)^{d,e}$ | Zeta Potental, $mV^f$ | HD, $nm^g$ | $QY^h$ |
|---|---|---|---|---|---|---|---|---|
| 1 | 13,500 | 1.30 | 16 | 434 | 490 | 8.0 ± 2.0 | 99 ± 29 | 8.0 |
| 2 | 13,800 | 1.40 | 15 | 434 | 494 | 4.0 ± 1.0 | 139 ± 43 | 20 |

[a] Determined by gel permeation chromatography in THF,
[b] Polydispersity index (Mw/Mn),
[c] Degree of polymerization,
[d] Measured in DMSO,
[e] Excitation wavelength 430 nm,
[f] Zeta potential in water,
[g] Determined by nanoparticle tracking analysis,
[h] Quantum yield in DMSO measured relative to diphenylanthracene standard

TABLE 2

Size in nm of Poly-1 and Poly-2 with siRNA

| Poly | Polymer, $nm^{a,b}$ | Polymer-siRNA, $nm^{a,b}$ |
|---|---|---|
| 1 | 99 ± 29 | 137 ± 40 |
| 2 | 139 ± 43 | 152 ± 44 |

[a] DMSO (1%) and water (99%),
[b] Conc. of final polymer and siRNA were 1 μM and 10 nM, respectively Zeta potentials of Poly-1 and Poly-2 in complexation with siRNA were measured using Zetasizer Nano-ZS (Zen 3600, Malvern Instruments Ltd.). The viscosity and refractive index of water were used for estimation of relative zeta potential difference among the samples. Stock polymer samples were prepared at a concentration of 1000 μM in DMSO. 10 μL of stock polymer solution was dissolved in 90 μL RNAse water. Then the polymer solution in RNAse water was transferred to 900 μL of siRNA containing RNAse water (siRNA concentration 11.11 nM) and the solution was mixed by pipetting. The final polymer and siRNA concentration in the solution were 10 μM and 100 nM, respectively. All measurements were performed in triplicates at 25° C. and the average values were reported in Table 3, below.

TABLE 3

Zeta potential of Poly-1 and Poly-2 with siRNA

| Poly | Polymer, $mV^a$ | Polymer-siRNA, $mV^b$ |
|---|---|---|
| 1 | 8.0 ± 2 | 11 ± 1.3 |
| 2 | 4.0 ± 1 | 12 ± 0.8 |

[a] DMSO (1%) and water (99%),
[b] Conc. of final polymer and siRNA were 1 μM and 10 nM Cell Culture Primary human bronchial epithelial cells were isolated and re-differentiated at the air-liquid interface cultures as per Unwalla et al. *Am. J. Respir. Cell. Mol. Biol.* 2012, 46(4), 551-8 and Unwalla et al. *Am. J. Respir. Cell. Mol. Biol.* 2015, 52 (1), 65-74. Cells were obtained from properly consented donors whose lungs were not suitable for transplantation for the causes unrelated to airway complications and supplied by University of Miami Life Alliance Organ Recovery Agency. Since the material was obtained from deceased individuals with minor, de-identified information, its use does not constitute human subjects research as defined by CFR 46.102. A signed and well documented consent of each individual or legal healthcare proxy for the donation of lungs for research purpose is on file with the Life Alliance Organ Recovery Organization allows research purpose of this material. Unless otherwise indicated, experiments used cells from non-smokers to not confound the findings in unknown ways. These primary cultures undergo mucociliary differentiation at the air-liquid interface reproducing in vivo morphology and key physiologic processes to recapitulate the native bronchial epithelium ex vivo. Primary NHBE cells isolated from human lungs were provided by University of Miami Life Alliance Organ Recovery Agency and re-differentiated on porous supports at the air-liquid interface. Re-differentiated NHBE cells were tested for ciliation by staining acetylated tubulin.

The immortalized normal human bronchial epithelial cell line BEAS-2B (ATCC CRL-9609) was purchased from the American Type Culture Collection (Manassas, Va., USA). BEAS-2B cells were cultured in BioLite 75 cm² flasks (Thermo Scientific) containing Bronchial Epithelial Cell Growth Medium (BEGM). BEGM media was supplemented with 0.1% (v/v) human recombinant epidermal growth factor, 0.1% (v/v) insulin, 0.1% (v/v) hydrocortisone, 0.1% (v/v) ethanolamine, 0.1% phosphoryl ethanolamine, 0.1% (v/v) retinoic acid, 0.1% (v/v) epinephrine, 0.24% (v/v) transferrin, 1% (v/v) penicillin/streptomycin and 0.1% (v/v) bovine pituitary extract. The cells were cultured in 95% air and 5% C02 at 37° C. and maintained free of *mycoplasma* contamination.

Cell Viability Assay

BEAS-2B cells (~15,000 cells per well) in 200 μL of a complete medium, were seeded into a 96-well plate and allowed to attach for one day at 37° C. under humidified atmosphere of 5% CO2/95% air. Final concentrations of 40 μM, 20 μM, 10 μM, 5 μM, and 1 μM of CPs were added into the complete media by dilution with CPs stock solutions. After addition of CPs, cells were incubated for another 18 h. The cells were treated with 10 μL of methylthiazole tetrazolium (MTT) (5 mg/mL in PBS, CALBIOCHEM, Germany) and incubated for 4 h at 37° C. Subsequently, 200 μL of medium was removed by using a pipette and then 100 μL of biological grade DMSO (Sigma Aldrich, St. Louis, Mo., USA) was added to solubilize the purple formazan crystals formed by proliferating cells. Absorbance was measured by a microplate well reader (infinite M1000 PRO, TECAN, Switzerland) at 570 nm. Relative cell viability (%), FIG. 9, as a function of CPs concentration was expressed as the percentage relative to the untreated control cells. All measurements were performed in triplicate and standard deviation was included in the error bar.

Gel Retardation Assay

The siRNA binding capabilities of Poly-1 and Poly-2, respectively, were examined by a gel retardation assay as indicated in FIG. 10. 10 μL of siHDAC (400 nM) (Santa Cruz Biotechnology) was mixed with 10 μL of the polymers with different concentrations. Samples were gently vortexed and kept for 30 m at room temperature. Then, polyplexes solutions (20 μL) were mixed with 20 μL of 2×RNA loading buffer (Thermo Fisher Scientific). The polyplexes solutions (40 μL) were loaded in to 40% poly (acrylamide) gel (cross-linking of 2.67) and run in 1×TBE buffer at 90V for 80 m. Free siHDAC bands were visualized using 0.5 μg/mL ethidium bromide solution. The bands were visualized by using the Quantity One software (Bio-Rad Laboratories, USA) and the density values are normalized to free siRNA.
Immunocytochemistry for Cilia to Determine Differentiation.

NHBE cells were allowed to re-differentiate for 21 days at the air-liquid interface on transwell filters. Re-differentiation was determined by staining for ciliation as described in Chinnapaiyan et al. *PLoS One* 2017. 12(1): p. e0169161. Cells were fixed in 4% paraformaldehyde in PBS, pH 7.4 for 15 min and permeabilized with 1% Triton X-100 in PBS for 20 min at room temperature (RT). After permeabilization, cells were washed with PBS and then blocked with 3% BSA in PBS for 1 h at room temperature. Cells were treated with the primary antibody [mouse anti human acetylated α-tubulin (Sigma Cat. #T6793; 1:1000)] in blocking solution and incubated overnight at 4° C. Cells were washed three times and then incubated with Alexa 647 anti mouse IgG for 45 min. Cells were washed three times with blocking solution and counterstained with 4,6-diamidine-2-phenylindole (DAPI, KPL) to label nuclei for 10 min. Transwell filters were excised and placed directly on the slide and images were acquired on visualized using a Zeiss fluorescence microscope with high resolution Axiocam 506 mono microscope camera (Zeiss, Germany). Cilia appear green at the apical side of the NHBE cultures with nuclei stained in blue.
Confocal Microscopic Images of BEAS-2B Cells.

BEAS-2B cells (~0.5×10$^6$/well) were seeded into a 12-well plate with glass coverslip one day prior to CP treatment, and then cultured in a complete media for 24 h under 5% $CO_2$ at 37° C. Cells were washed three times with 1×PBS after removing the media. The polyplex formed by mixing 10 μM CPs and siGLO (100 nM) was added to cells and then incubated for 48 h. After 48 h incubation, cells were washed three times with 1×PBS and fixed with 4% PFA for 10 m. Cells were then washed three times with 1×PBS and coverslips were mounted on microscope slides using a 1:1 glycerol/PBS mounting medium. Fluorescent images of the cells were obtained using an Olympus Fluorview FV1200 confocal microscope (Melville, N.Y. USA) equipped with a bandpass filter for green (513-556 nm) and a 60× oil immersion len (NA 1.35, n=1.519 immersion oil). Image J software (Version 1.50b, U.S. National Institute of Health, Bethesda, Md., USA) was used to process the image.
Confocal Fluorescence Microscopic Images of Primary NHBE Cells.

NHBE cells were treated with polyplex containing siGLO as described, above. After 48 h incubation, cells were washed three times with 1×PBS and fixed with 4% PFA for 10 m. Cells were then washed three times with 1×PBS. The cells grown on semipermeable membrane were separated from the chamber and then mounted on a microscope slide using a 1:1 glycerol/PBS mounting medium followed by sealing with nail polish. Fluorescent images of the cells were obtained using an Olympus Fluorview FV1200 confocal microscope (Melville, N.Y. USA) equipped with a bandpass filter (513-556 nm) and a 60× oil immersion lens (NA 1.35). Image J software (Version 1.50b, U.S. National Institute of Health, Bethesda, Md., USA) was used to process the image.

Gene Knockdown Experiment in BEAS-2B Cells
Lipofectamine RNAiMAX-Mediated Transfection of siHDAC in BEAS-2B Cells.

High-capacity cDNA reverse transcription kit was purchased from Applied Biosystems. Taqman Fast Advanced Master Mix was purchased from Life Technologies. Lipofectamine® RNAiMAX Transfection Reagent and Opti-MEM™ Reduced-Serum Medium were purchased from Thermo Fisher Scientific. BEAS-2B cells were plated on collagen coated tissue culture plates at a density of 0.6×10$^6$. Twenty-four hours following plating, cells were transfected with siHDAC complexed with Lipofectamine RNAiMax in Opti-MEM medium according to manufacturer's instructions using different concentrations of the siRNA (i.e., 12.5, 25, 50, 75, and 100 nM). BEAS-2B cells treated with equivalent amounts of lipofectamine RNAiMAX in Opti-MEM was used as transfection control, as shown in FIG. 13. The mixture was vortexed and incubated at room temperature for 30 m before adding to the cells. After eight-hour post-transfection, experiments were terminated, and total RNA was isolated and analyzed by quantitative RT-PCR.
Polymer-Mediated Transfection of siHDAC in BEAS-2B Cells.

The polyplex solutions were freshly prepared prior to transfection experiments. One day after plating BEAS-2B cells (0.6×10$^6$) in a 12-wells plate, cells were transfected by adding polyplex solutions. 5 mM polymer stock solution was diluted to 5, 10, 20, and 40 μM, respectively, in 50 μl of RNase and DNase free water, and then mixed with various amounts of siHDAC (i.e., 12.5, 25, 50, 75, and 100 nM). Polyplex solution was vortexed for 30 m. Cells were incubated with polyplex for 48 h. The total RNA was analyzed by quantitative RT-PCR, as indicated in FIG. 13.
Gene Knockdown Experiment in NHBE Cells The polyplex solutions were freshly prepared prior to transfection experiments. NHBE cultures re-differentiated at the air-liquid interface (ALI) were transfected by adding polyplex solutions using a protocol identical to that for BEAS2B cells above. Separately, another set of NHBE air-liquid interface cultures were treated with siRNA complexed with Lipofectamine RNAimax for comparison. Experiments proceeded for 48 hours and total RNA was isolated and analyzed by quantitative RT-PCR, as indicated in FIG. 13.

Total RNA was extracted from cells treated with transfection agents after 48 h incubation using an RNeasy mini kit (Qiagen Inc. Valencia, Calif.). The concentration and integrity of the extracted RNA were analyzed by measurement of the OD260/280 (Synergy™ HTX Multi-Mode Microplate Reader, Winooski, Vt., USA). Complementary DNA (cDNA) was reversely transcribed by using the Applied Biosystems High performance kit (Applied Biosystem, Carlsbad, Calif.). Reverse transcription of 2 μg of total cellular RNA was performed in a final volume of 20 μl containing 10 μl of RNA, 2 μl of 10×RT buffer, 0.8 μl of dNTP Mix (100 mM), 2.0 μl of 10×RT random hexamer primers, 1.0 μl of MultiScribe™ reverse transcriptase, 1 μl of RNase inhibitor, and 3.2 μl of nuclease-free water. The reverse transcription reaction was allowed to proceed using cycling parameters recommended by the manufacturer: an initial incubation at 25° C. for 10 m followed by incubation at 37° C. for 120 m. The reverse transcription was terminated by incubating at 85° C. for 5 sec. cDNA samples were stored at −20° C. until further use for quantitative PCR. Quantitative PCR was performed on the Bio-Rad CFX96 real-time system (BioRad, Hercules, Calif., USA) using validated TaqMan probes (GAPDH, HDAC2) according to manufacturer recommended cycling parameters (an initial denaturation cycle of 95° C. for 20 s followed by 40 cycles of 95° C./3 s and 60° C./30 s. qRT-PCR results are represented as relative quantification normalized to internal control (GAPDH).

Ussing Chamber Method to Determine Apical CFTR Activity

Ussing chamber electrophysiology was used to confirm re-differentiation and polarization as per: Unwalla et al., *Am. J. Respir. Cell. Mol. Biol.* 2015, 52 (1), 65-74; and Chinnapaiyan et al., *Sci Rep.* 2018, 8(1), 7984. CFTR is located at the apical side (mucosal) of the airway epithelium. Briefly, NHBE cultures were re-differentiated at the air-liquid interface. Following re-differentiation for 21 days, the snap wells were removed from supports and mounted in Ussing chambers. The short circuit current was measured and allowed to stabilize followed by addition of amiloride (10 µM) added apically to eliminate epithelial sodium channel (ENaC) influences. CFTR activation was affected by addition of albuterol (10 µM) and change in short circuit current ($\Delta I_{SC}$) was determined. CFTR specificity was confirmed by addition of CFTR inhibitor $CFTR_{inh}172$ (20 µM) and the decrease in $\Delta I_{SC}$ was recorded.

Protein Delivery

Various homopolymers, random copolymers and block copolymers of the subject invention have been synthesized for the intracellular delivery of proteins. The role of the guanylurea functional group was explored by comparing the PN-G as a guanidine-rich control, PN-G-BA that contains a hydrophobic phenyl moiety directly attached on the positive charged side chain through guanylurea modification, and a copolymer variant, PN-co-G-BA, which isolates the phenyl groups from the positive charge by having the two on isolated repeating units. The chain length of polymers PN-G-BA and PN-co-G-BA was controlled to have the same number of positive charges and same relative hydrophobicity since these may be factors that influence the protein complexation and cellular entry.

To understand the ability of the synthesized polymers on protein delivery and the role of the guanylurea functionality, EGFP delivery into Hela cells was chosen as a model system. In short, the polymers were mixed with EGFP at ratios of 10 uM and 60 nM respectively. The complexes were allowed to form for 30 minutes prior to treating Hela cells in serum containing medium. Hela cells were treated overnight with complexes, and rinsed thoroughly with PBS prior to flow cytometric analysis.

Figure 20:
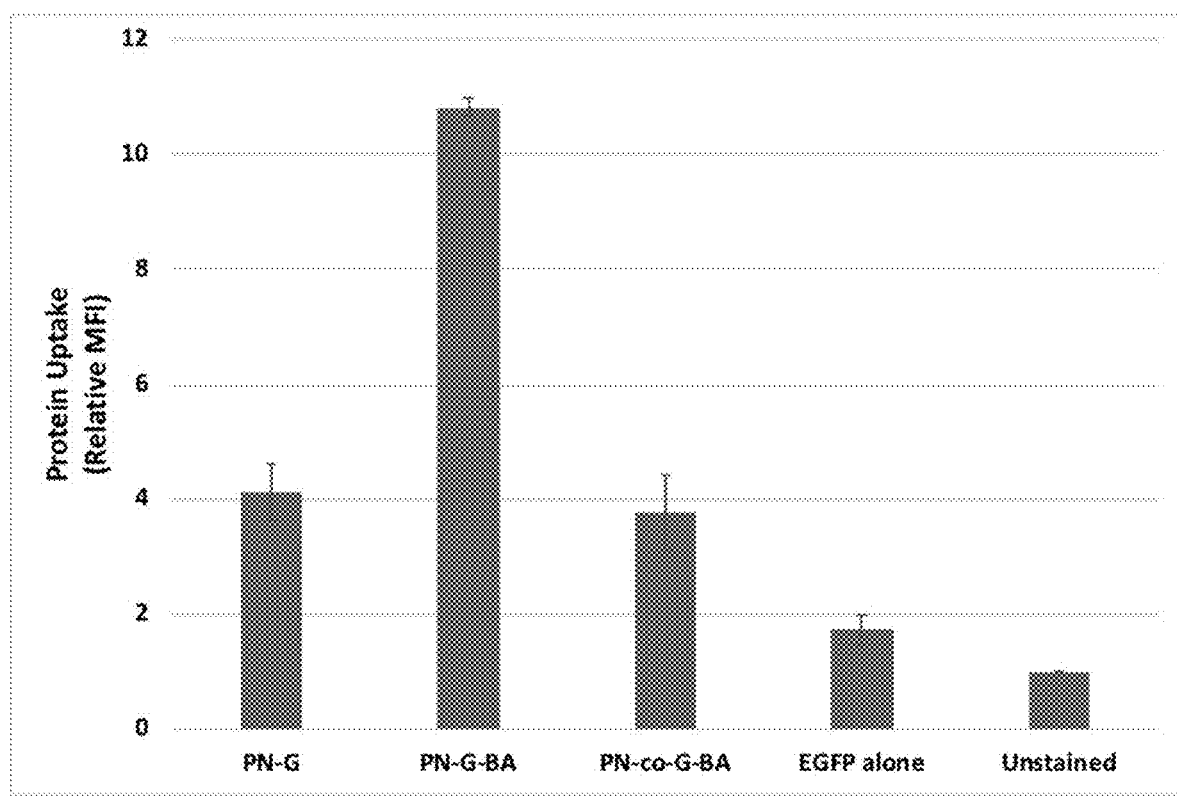
FIG. 20 shows the flow cytometric analysis of Hela cells treated with polymers (10 µM)/Enhanced Green Fluorescent Protein (EGFP) (60 nM) complexes overnight at 37° C. in serum containing medium. Values represent the mean relative MFI as compared to untreated cells ±CV for two independent experiments.

Results show ~3 fold improvement in delivery efficiency using the guanylurea modified polymer, PN-G-BA, as compared to the other polymers (FIG. 20). PN-co-G-BA containing the same degree of hydrophobicity as PN-G-BA shows similar delivery efficiency as the guanidine rich polymer PN-G (FIG. 20). This result indicates that the guanylurea modification that maintains the hydrophobic segment on the positive charge exhibits the best EGFP delivery efficiency.

Various homopolymers, random copolymers and block copolymers containing boronic acid moieties may be used as a targeted therapy for cancer treatments. Improvements in cell entry efficiency, cargo complexation and nanoparticle stability are explored with these polymeric systems.

All patents and publications referred to or cited herein are incorporated by reference in their entirety, including all figures and tables, to the extent they are not inconsistent with the explicit teachings of this specification.

It should be understood that the examples and embodiments described herein are for illustrative purposes only and that various modifications or changes in light thereof will be suggested to persons skilled in the art and are to be included within the spirit and purview of this application.

We claim:

1. A modulated guanidine substituted polymer, comprising a guanidine moiety on a plurality of repeating units of a polymer, the repeating unit comprises the following structure:

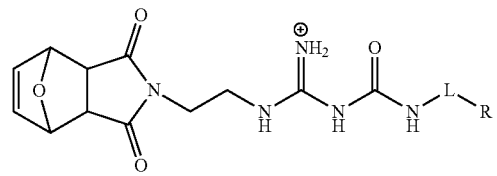

wherein L is a linker and can be null; and R is selected from hydrogen, alkyl, substituted alkyl, aryl, substituted aryl, heteroaryl, substituted heteroaryl, heteroalkyl, substituted heteroalkyl, cycloalkyl, substituted cycloalkyl, heterocycloalkyl, substituted heterocycloalkyl, cycloalkenyl, and substituted cycloalkenyl, alkenyl and substituted alkenyl, alkynyl, haloalkyl, acyl, amino, alkylamino, arylamino and hydroxylalkyl.

2. The modulated guanidine substituted polymer according to claim 1, R being an N-alkylamino; N-arylamino; N-(alkylaryl)amino; N-(aryalkyl)amino; N, N-dialkylamino; N, N-diarylamino; N, N-di(alkylaryl)amino; N, N-di(aryalkylamino); N-alkyl,N-arylamino; N-alkyl,N-(alkylaryl)amino; N-alkyl,N-(arylalkyl)amino; N-aryl,N-(alkylaryl)amino; or N-aryl,N-(arylalkyl)amino group.

3. The modulated guanidine substituted polymer according to claim 1, R being an unsubstituted or substituted morpholine, pyrolidine, pyrrole, piperidine, ethyleneimine, indole, isoindole, carbazole, imidazole, purine, aminoethanol, amino terminal polyethylene oxide, substituted or unsubstituted alky carbamate, substituted or unsubstituted aryl carbamate, substituted or unsubstituted alkylaryl carbamate, or substituted or unsubstituted aryalkyl carbamante.

4. The modulated guanidine substituted polymer according to claim 1, R being selected from hexylamine (HA), benzylamine (BA), and aminoethoxyethanol (AEE).

5. The modulated guanidine substituted polymer according to claim 1, the polymer being a homopolymer having a structure of

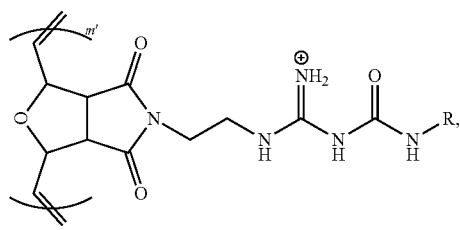

wherein m'≥2; and R is selected from hexylamine (HA), benzylamine (BA), and aminoethoxyethanol (AEE).

6. The modulated guanidine substituted polymer according to claim 1, the polymer being a copolymer, the copolymer further comprising one or more types of monomer species selected from

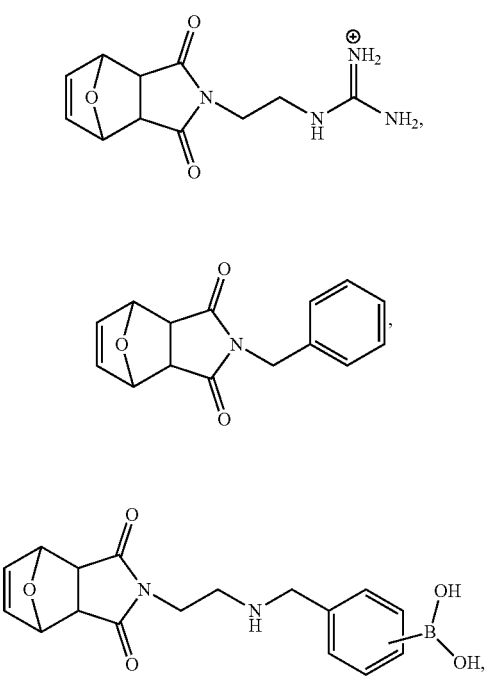

and

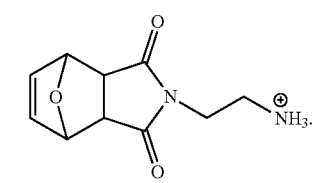

7. The modulated guanidine substituted polymer according to claim 6, the copolymer being a random copolymer selected from

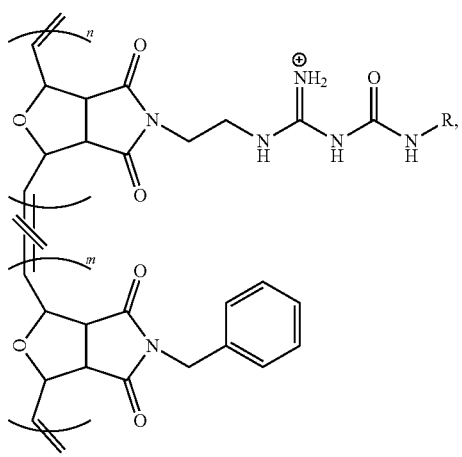

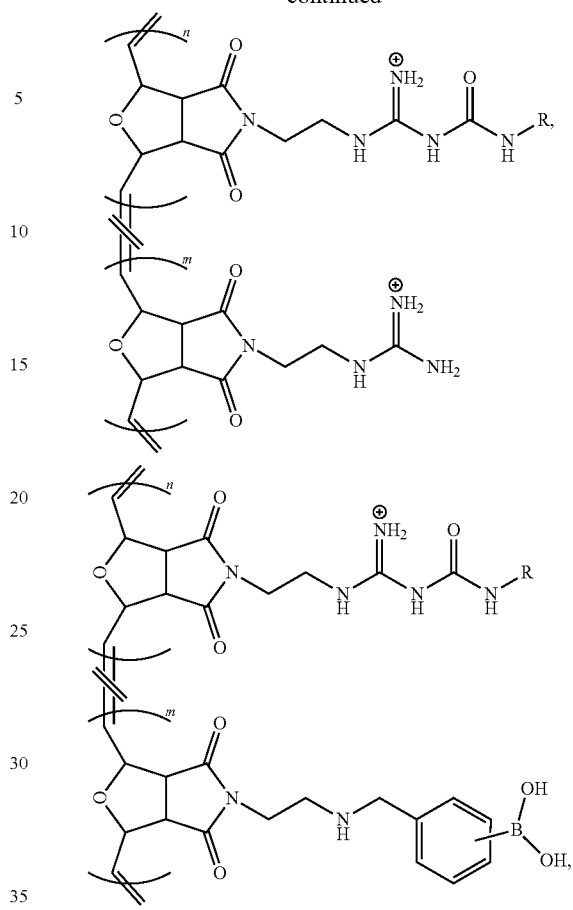

and

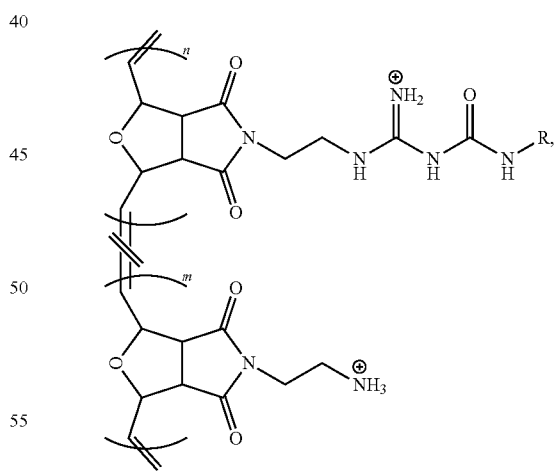

wherein ⇌ means that the two monomer species are randomly distributed; both m and n≥1; R is selected from hexylamine (HA), benzylamine (BA), and aminoethoxyethanol (AEE).

8. The modulated guanidine substituted polymer according to claim 6, the copolymer being a block copolymer comprising a structure of

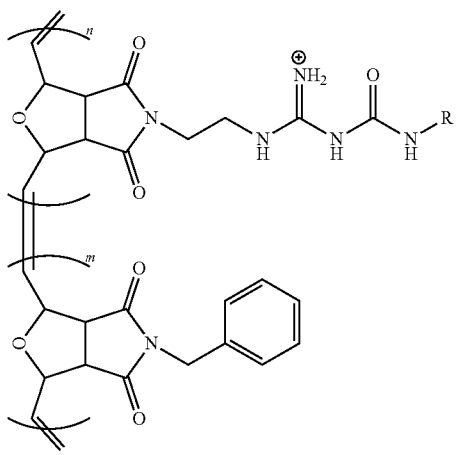

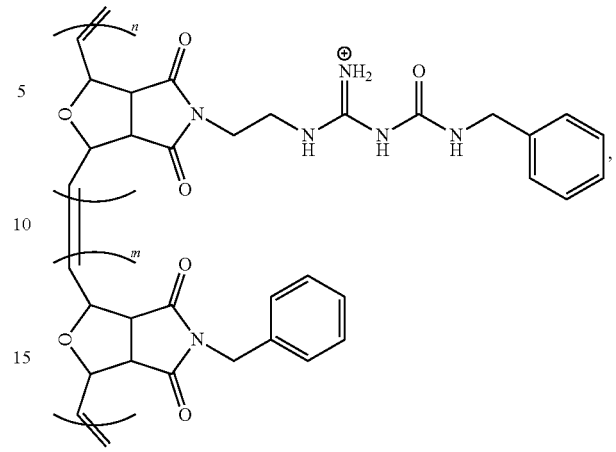

wherein m and n can be the same or different, and both m and n≥1; and R is selected from hydrogen, alkyl, substituted alkyl, aryl, substituted aryl, heteroaryl, substituted heteroaryl, heteroalkyl, substituted heteroalkyl, cycloalkyl, substituted cycloalkyl, heterocycloalkyl, substituted heterocycloalkyl, amino, alkylamino, arylamino and hydroxylalkyl.

9. The modulated guanidine substituted polymer according to claim 8, the block copolymer being selected from wherein m and n≥1, and m and n can be the same or different.

10. The modulated guanidine substituted polymer according to claim 6, the copolymer being a block copolymer comprising a structure of

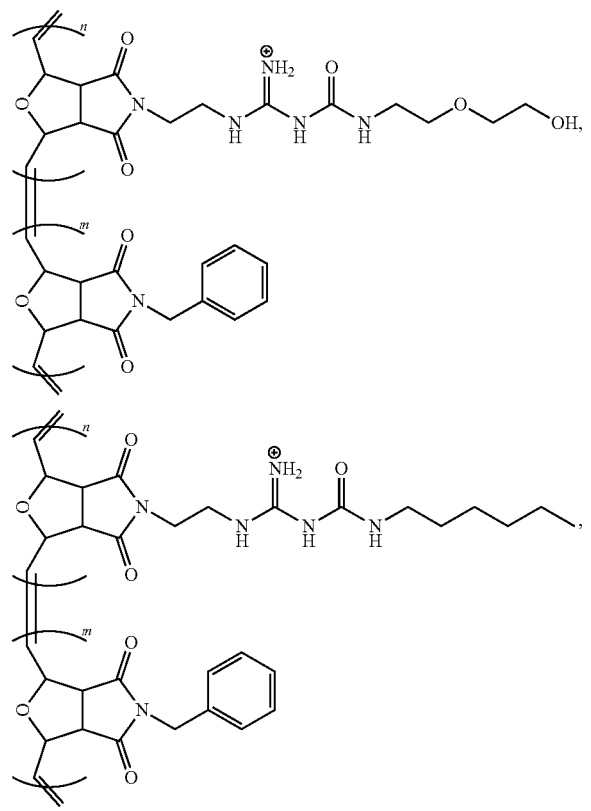

and

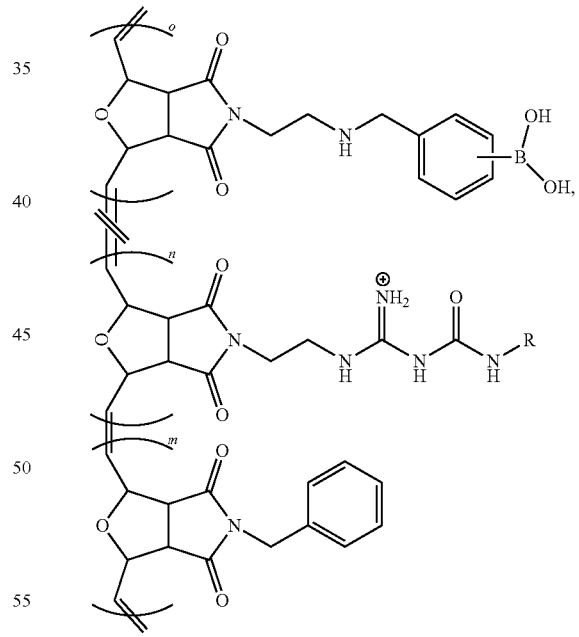

wherein ⌇⌇ means that the two monomer species are randomly distributed; m, n and o can be the same or different, and m, n and o≥1; and R is selected from hydrogen, alkyl, substituted alkyl, aryl, substituted aryl, heteroaryl, substituted heteroaryl, heteroalkyl, substituted heteroalkyl, cycloalkyl, substituted cycloalkyl, heterocycloalkyl, substituted heterocycloalkyl, amino, alkylamino, arylamino and hydroxylalkyl.

11. The modulated guanidine substituted polymer according to claim 10, the block copolymer being selected from

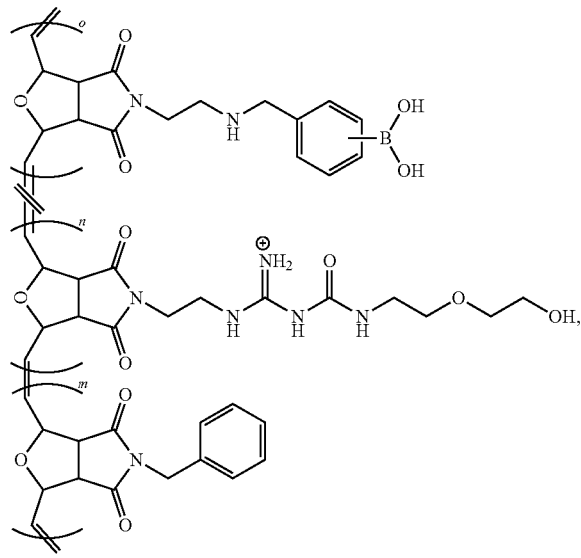

and

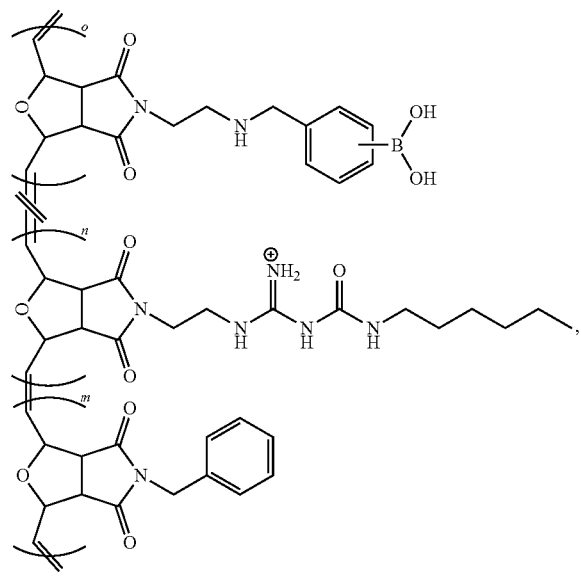

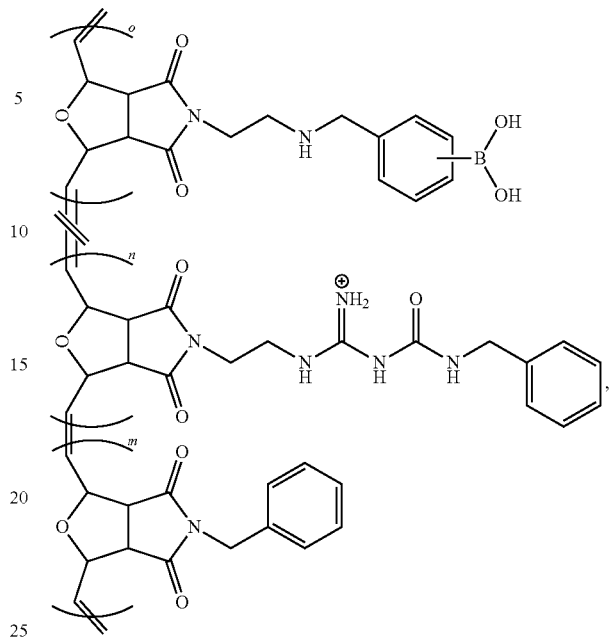

wherein m, n and o≥1, and m, n and o can be the same or different; ⫽ means that the two monomer species are randomly distributed.

12. The modulated guanidine substituted polymer according to claim 6, the copolymer being a block copolymer comprising a boronic acid moiety on the modulated guanidine moiety.

13. The modulated guanidine substituted polymer according to claim 12, the block copolymer having a structure of

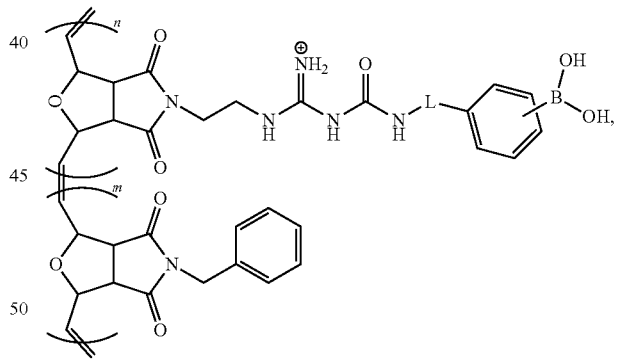

wherein m and n≥1, and m and n can be the same or different; and L is a linker and can be null.

14. The modulated guanidine substituted polymer according to claim 13, the linker being a C1-C10 alkyl or heteroalkyl.

15. The modulated guanidine substituted polymer according to claim 1, which is conjugated to a nanoparticle, the nanoparticle comprising silica, alumina, titania, zinc oxide, tin oxide, silver oxide, cuprous oxide, cupric oxide, ceria, vanadium oxide zirconia, molybdenum, tungsten oxide, barium oxide, calcium oxide, iron oxide, or nickel oxide.

16. A therapeutic formulation comprising the modulated guanidine substituted polymer of claim 1, a therapeutic agent and a pharmaceutically acceptable carrier.

17. A method for treating cancer comprising administering, to a subject in need of such treatment, an effective amount of the therapeutic formulation of claim 16.

18. A method for delivering a therapeutic agent into a cancer cell, comprising contacting the cancer cell with the modulated guanidine substituted polymer of claim 1, and the therapeutic agent.

19. A method for transporting a therapeutic agent across a biological membrane, comprising contacting the biological membrane with the modulated guanidine substituted polymer of claim 1, and the therapeutic agent.

20. A method according to claim 19, the biological membrane being selected from cell membranes, organelle membranes, mucous membranes, basement membranes, and serous membranes.

\* \* \* \* \*

UNITED STATES PATENT AND TRADEMARK OFFICE
CERTIFICATE OF CORRECTION

PATENT NO.         : 10,688,189 B1
APPLICATION NO.    : 16/799375
DATED              : June 23, 2020
INVENTOR(S)        : Joong Ho Moon and Alfonso Barrios Page 1 of 1

It is certified that error appears in the above-identified patent and that said Letters Patent is hereby corrected as shown below:

On the Title Page

"(73) Assignee: THE FLORIDA INTERNATIONAL BOARD OF TRUSTEES, Miami, FL (US)" should read -- (73) Assignee: THE FLORIDA INTERNATIONAL UNIVERSITY BOARD OF TRUSTEES, Miami, FL (US) --

Signed and Sealed this
Eighth Day of February, 2022

Drew Hirshfeld
*Performing the Functions and Duties of the
Under Secretary of Commerce for Intellectual Property and
Director of the United States Patent and Trademark Office*